(12) United States Patent
Cao et al.

(10) Patent No.: US 11,353,602 B2
(45) Date of Patent: Jun. 7, 2022

(54) BONDING MATERIALS OF DISSIMILAR COEFFICIENTS OF THERMAL EXPANSION

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 65 days.

(21) Appl. No.: 16/690,853

(22) Filed: Nov. 21, 2019

(65) Prior Publication Data
US 2020/0086412 A1 Mar. 19, 2020

Related U.S. Application Data

(60) Division of application No. 16/160,247, filed on Oct. 15, 2018, now Pat. No. 10,518,346, which is a continuation of application No. PCT/CN2016/088514, filed on Jul. 5, 2016.

(51) Int. Cl.
| | | |
|---|---|---|
| *G01T 1/24* | (2006.01) |
| *H01L 21/20* | (2006.01) |
| *B23K 1/00* | (2006.01) |
| *A61B 6/00* | (2006.01) |
| *G03B 42/02* | (2021.01) |
| *B23K 101/40* | (2006.01) |
| *B23K 3/08* | (2006.01) |
| *H01L 27/146* | (2006.01) |

(52) U.S. Cl.
CPC ............ *G01T 1/244* (2013.01); *A61B 6/4241* (2013.01); *G01T 1/246* (2013.01); *G01T 1/247* (2013.01); *B23K 1/0016* (2013.01); *B23K 3/08* (2013.01); *B23K 2101/40* (2018.08); *G03B 42/02* (2013.01); *H01L 21/2007* (2013.01); *H01L 27/14658* (2013.01)

(58) Field of Classification Search
None
See application file for complete search history.

(56) References Cited

U.S. PATENT DOCUMENTS

| | | | | |
|---|---|---|---|---|
| 3,891,822 A * | 6/1975 | Laub | ................. | B23K 20/005 |
| | | | | 219/85.18 |
| 4,481,403 A | 11/1984 | Del Monte | | |
| 6,054,693 A * | 4/2000 | Barmatz | ................ | B23K 1/002 |
| | | | | 219/678 |
| 8,381,966 B2 * | 2/2013 | Kumar | ................. | B23K 1/0016 |
| | | | | 228/180.22 |

(Continued)

FOREIGN PATENT DOCUMENTS

| | | |
|---|---|---|
| CN | 102283668 A | 12/2011 |
| JP | 2014200819 A | 10/2014 |

(Continued)

*Primary Examiner* — Devang R Patel
(74) *Attorney, Agent, or Firm* — IPro, PLLC; Qian Gu

(57) ABSTRACT

Disclosed herein is an X-ray detector comprises: an X-ray absorption layer configured to absorb X-ray photons; an electronics layer comprising an electronics system configured to process or interpret signals generated by the X-ray photons incident on the X-ray absorption layer; and a temperature driver in the X-ray absorption layer or the electronics layer.

5 Claims, 26 Drawing Sheets

(56) References Cited

U.S. PATENT DOCUMENTS

| | | | |
|---|---|---|---|
| 10,058,952 B2* | 8/2018 | Seok | B23K 20/26 |
| 2003/0043959 A1 | 3/2003 | Wischmann et al. | |
| 2003/0178474 A1* | 9/2003 | Jiang | H01L 21/563 |
| | | | 228/205 |
| 2011/0318918 A1* | 12/2011 | Kitamura | H01L 24/11 |
| | | | 438/614 |

FOREIGN PATENT DOCUMENTS

| | | |
|---|---|---|
| TW | 200941716 A | 10/2009 |
| TW | 201519349 A | 5/2015 |
| TW | 201534476 A | 9/2015 |

\* cited by examiner

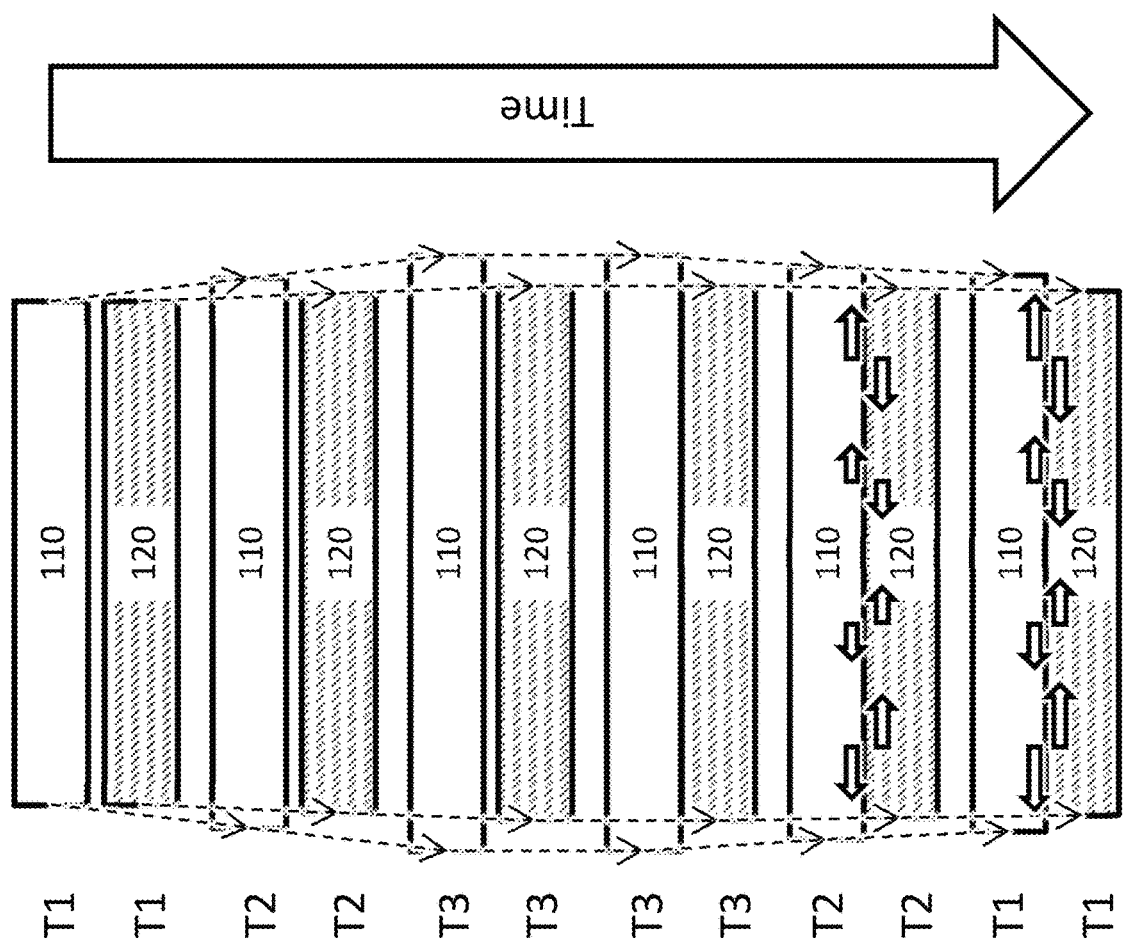

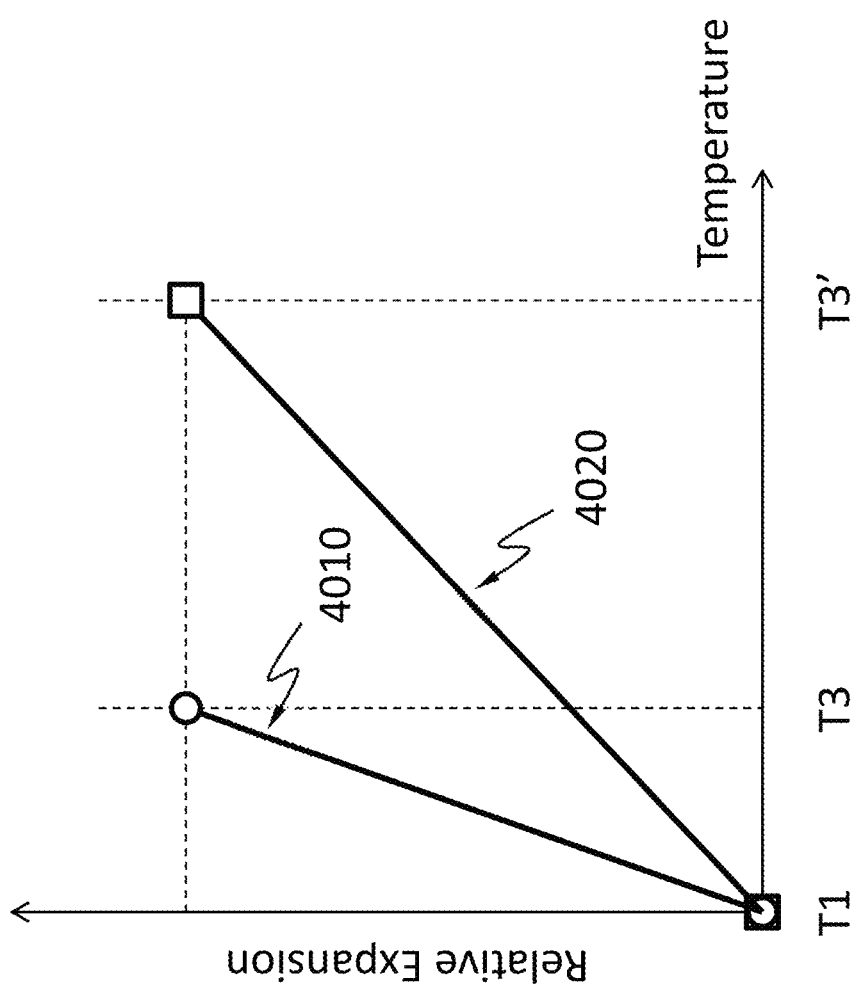

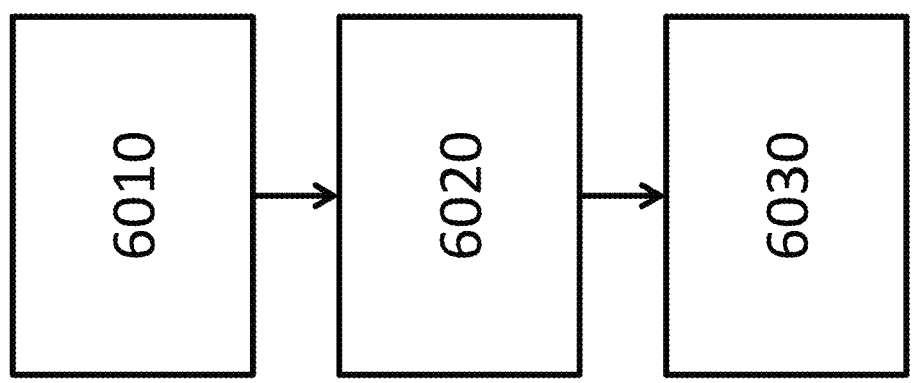

BONDING MATERIALS OF DISSIMILAR COEFFICIENTS OF THERMAL EXPANSION

TECHNICAL FIELD

The disclosure herein relates to bonding materials of dissimilar coefficients of thermal expansion, such as GaAs and silicon, which may be used in x-ray detectors.

BACKGROUND

X-ray detectors may be devices used to measure the flux, spatial distribution, spectrum or other properties of X-rays.

X-ray detectors may be used for many applications. One important application is imaging. X-ray imaging is a radiography technique and can be used to reveal the internal structure of a non-uniformly composed and opaque object such as the human body.

Early X-ray detectors for imaging include photographic plates and photographic films. A photographic plate may be a glass plate with a coating of light-sensitive emulsion. Although photographic plates were replaced by photographic films, they may still be used in special situations due to the superior quality they offer and their extreme stability. A photographic film may be a plastic film (e.g., a strip or sheet) with a coating of light-sensitive emulsion.

In the 1980s, photostimulable phosphor plates (PSP plates) became available. A PSP plate may contain a phosphor material with color centers in its lattice. When the PSP plate is exposed to X-ray, electrons excited by X-ray are trapped in the color centers until they are stimulated by a laser beam scanning over the plate surface. As the plate is scanned by laser, trapped excited electrons give off light, which is collected by a photomultiplier tube. The collected light is converted into a digital image. In contrast to photographic plates and photographic films, PSP plates can be reused.

Another kind of X-ray detectors are X-ray image intensifiers. Components of an X-ray image intensifier are usually sealed in a vacuum. In contrast to photographic plates, photographic films, and PSP plates, X-ray image intensifiers may produce real-time images, i.e., not requiring postexposure processing to produce images. X-ray first hits an input phosphor (e.g., cesium iodide) and is converted to visible light. The visible light then hits a photocathode (e.g., a thin metal layer containing cesium and antimony compounds) and causes emission of electrons. The number of emitted electrons is proportional to the intensity of the incident X-ray. The emitted electrons are projected, through electron optics, onto an output phosphor and cause the output phosphor to produce a visible-light image.

Scintillators operate somewhat similarly to X-ray image intensifiers in that scintillators (e.g., sodium iodide) absorb X-ray and emit visible light, which can then be detected by a suitable image sensor for visible light. In scintillators, the visible light spreads and scatters in all directions and thus reduces spatial resolution. Reducing the scintillator thickness helps to improve the spatial resolution but also reduces absorption of X-ray. A scintillator thus has to strike a compromise between absorption efficiency and resolution.

Semiconductor X-ray detectors largely overcome this problem by a direct conversion of X-ray into electric signals. A semiconductor X-ray detector may include a semiconductor layer that absorbs X-ray in wavelengths of interest. When an X-ray photon is absorbed in the semiconductor layer, multiple charge carriers (e.g., electrons and holes) are generated and swept under an electric field towards electrical contacts on the semiconductor layer. Cumbersome heat management required in currently available semiconductor X-ray detectors (e.g., Medipix) can make a detector with a large area and a large number of pixels difficult or impossible to produce.

SUMMARY

Disclosed herein is an X-ray detector comprises: an X-ray absorption layer configured to absorb X-ray photons; an electronics layer comprising an electronics system configured to process or interpret signals generated by the X-ray photons incident on the X-ray absorption layer; and a temperature driver in the X-ray absorption layer or in the electronics layer.

According to an embodiment, the X-ray detector further comprises a temperature sensor in the X-ray absorption layer or the electronics layer.

According to an embodiment, the temperature driver comprises a Peltier device.

According to an embodiment, the temperature driver comprises a resistive heater.

According to an embodiment, the temperature driver comprises individually addressable units.

According to an embodiment, the X-ray absorption layer or the electronics layer comprises a plurality of chips.

According to an embodiment, the electronics system comprises: a first voltage comparator configured to compare a voltage of the electrode to a first threshold; a second voltage comparator configured to compare the voltage to a second threshold; a counter configured to register a number of X-ray photons reaching the X-ray absorption layer; a controller; wherein the controller is configured to start a time delay from a time at which the first voltage comparator determines that an absolute value of the voltage equals or exceeds an absolute value of the first threshold; wherein the controller is configured to activate the second voltage comparator during the time delay; wherein the controller is configured to cause the number registered by the counter to increase by one, if the second voltage comparator determines that an absolute value of the voltage equals or exceeds an absolute value of the second threshold.

According to an embodiment, the electronics system further comprises a capacitor module electrically connected to the electrode of the first X-ray absorption layer, wherein the capacitor module is configured to collect charge carriers from the electrode of the first X-ray absorption layer.

According to an embodiment, the controller is configured to activate the second voltage comparator at a beginning or expiration of the time delay.

According to an embodiment, the electronics system further comprises a voltmeter, wherein the controller is configured to cause the voltmeter to measure the voltage upon expiration of the time delay.

According to an embodiment, the controller is configured to determine an X-ray photon energy based on a value of the voltage measured upon expiration of the time delay.

According to an embodiment, the controller is configured to connect the electrode of the first X-ray absorption layer to an electrical ground.

According to an embodiment, a rate of change of the voltage is substantially zero at expiration of the time delay.

According to an embodiment, a rate of change of the voltage is substantially non-zero at expiration of the time delay.

According to an embodiment, the X-ray absorption layer comprises a diode.

According to an embodiment, the X-ray absorption layer comprises GaAs, CdTe, CdZnTe, or a combination thereof and the electronics layer comprises silicon.

Disclosed herein is a method comprising: setting a layer of a first material to a first temperature; setting a layer of a second material to a second temperature, wherein the first material and the second material have different coefficients of thermal expansion; bonding the layer of the first material and the layer of the second material while the layer of the first material is at the first temperature and the layer of the second material is at the second temperature; changing temperatures of the layer of the first material and the layer of the second material toward a third temperature while maintaining relative thermal expansions of the layers essentially equal at all times before the layers reach the third temperature; wherein changing the temperatures of the layer of the first material and the layer of the second material toward the third temperature comprises using a temperature driver in the layer of the first material or the layer of the second material.

According to an embodiment, the layer of the first material and the layer of the second material are bonded by direct bonding or flip chip bonding.

According to an embodiment, the third temperature is below 40° C.

According to an embodiment, the layer of the first material is an X-ray absorption layer configured to absorb X-ray photons; wherein the layer of the second material is an electronics layer comprising an electronics system configured to process or interpret signals generated by the X-ray photons incident on the X-ray absorption layer.

Disclosed herein is a system for bonding a first layer and a second layer, comprising: a controller comprising a processor and a memory, the memory configured to store a program therein, the processor configured to control powers to a temperature driver in the second layer by executing the program; wherein the program, when executed, causes the processor to set powers to the temperature driver such that relative thermal expansions of the first layer and the second layer are essentially the same at all time during a process of bonding the first layer and the second layer.

According to an embodiment, the first layer is an X-ray absorption layer configured to absorb X-ray photons; wherein the second layer is an electronics layer comprising an electronics system configured to process or interpret signals generated by the X-ray photons incident on the X-ray absorption layer.

According to an embodiment, the second layer is mounted to a support and the controller controls the powers to the temperature driver through an electrical contact on the support.

According to an embodiment, the second layer comprises a temperature sensor.

According to an embodiment, the controller reads temperature of the second layer from the temperature sensor and controls the powers to the temperature driver in the second layer based on the temperature read from the temperature sensor.

Disclosed herein is a method comprising: positioning a chip to a location of a wafer, the wafer comprising a temperature driver therein, the temperature driver comprising a plurality of individually addressable units; bonding the chip to the wafer by changing a temperature of the location using the individually addressable units, without changing a temperature of another location of the wafer using the individually addressable units.

According to an embodiment, the chip is part of an X-ray absorption layer of an X-ray detector and the wafer is part of an electronics layer of the X-ray detector; wherein the X-ray absorption layer is configured to absorb X-ray photons and the electronics layer comprises an electronics system configured to process or interpret signals generated by the X-ray photons incident on the X-ray absorption layer.

According to an embodiment, the chip comprises a III-V semiconductor and the wafer comprises silicon.

According to an embodiment, the temperature of the location is changed such that solder bumps at the location are melted.

BRIEF DESCRIPTION OF FIGURES

FIG. 3A schematically shows thermal expansion of the X-ray absorption layer and the electronics layer during the bonding process if the X-ray absorption layer and the substrate of the electronics layer have substantially different coefficients of thermal expansion and the X-ray absorption layer and the electronics layer are always at the same temperature at any given moment during the bonding process.

FIG. 4B shows plots of the relative thermal expansion as a function of temperature of the X-ray absorption layer and the substrate of the electronics layer, respectively, before the X-ray absorption layer and the electronics layer are bonded.

FIG. 6 schematically shows a flow of a method of bonding the X-ray absorption layer and the electronics layer of the X-ray detector.

DETAILED DESCRIPTION

Figure 1A:
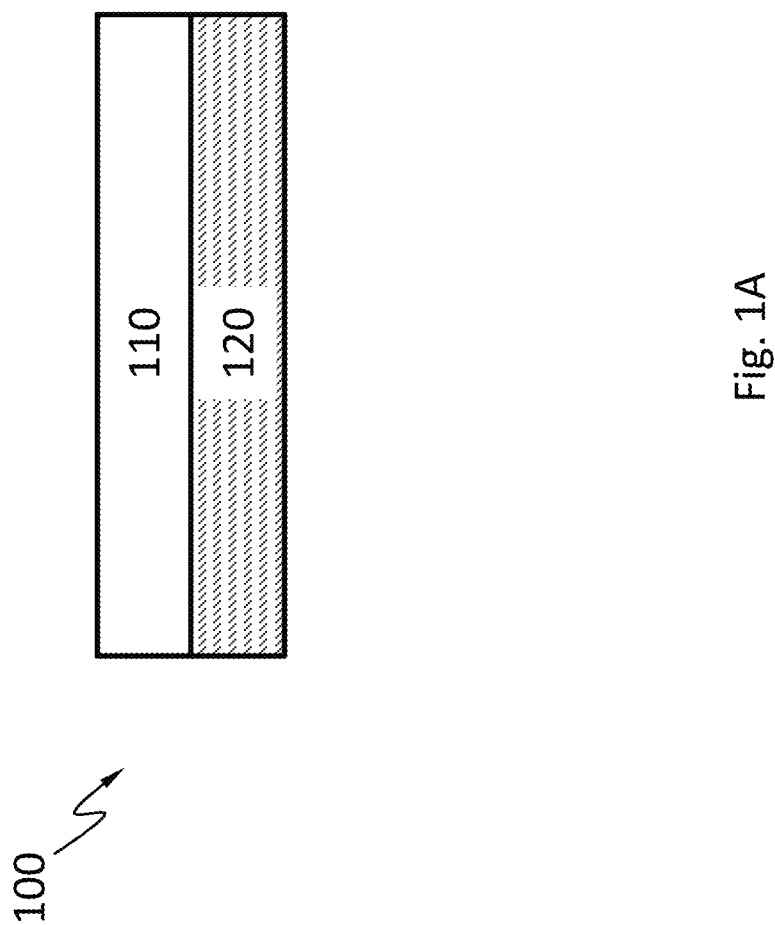
FIG. 1A schematically shows a cross-sectional view of a detector, according to an embodiment of the present teaching.

FIG. 1A schematically shows a semiconductor X-ray detector 100, according to an embodiment. The semiconductor X-ray detector 100 may include an X-ray absorption layer 110 and an electronics layer 120 (e.g., an ASIC) for processing or analyzing electrical signals incident X-ray generates in the X-ray absorption layer 110. In an embodiment, the semiconductor X-ray detector 100 does not comprise a scintillator. The X-ray absorption layer 110 may include a semiconductor material such as, silicon, germanium, GaAs, CdTe, CdZnTe, or a combination thereof. The semiconductor may have a high mass attenuation coefficient for the X-ray energy of interest.

Figure 1B:
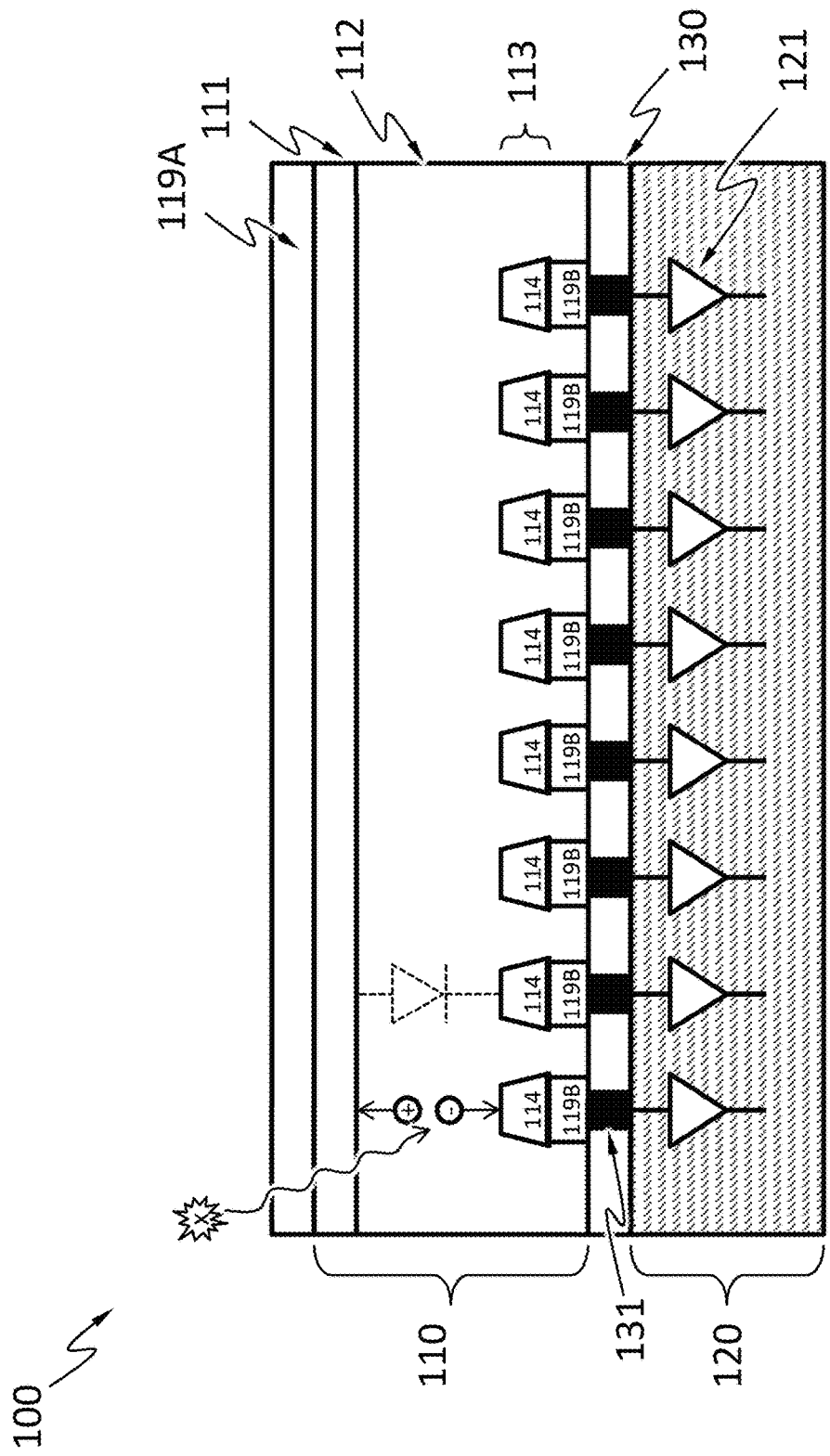
FIG. 1B schematically shows a detailed cross-sectional view of the detector, according to an embodiment of the present teaching.

As shown in a detailed cross-sectional view of the detector 100 in FIG. 1B, according to an embodiment, the X-ray absorption layer 110 may include one or more diodes (e.g., p-i-n or p-n) formed by a first doped region 111, one or more discrete regions 114 of a second doped region 113. The second doped region 113 may be separated from the first doped region 111 by an optional the intrinsic region 112. The discrete portions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 1B, each of the discrete regions 114 of the second doped region 113 forms a diode with the first doped region 111 and the optional intrinsic region 112. Namely, in the example in FIG. 1B, the X-ray absorption layer 110 has a plurality of diodes having the first doped region 111 as a shared electrode. The first doped region 111 may also have discrete portions.

When an X-ray photon hits the X-ray absorption layer 110 including diodes, the X-ray photon may be absorbed and generate one or more charge carriers by a number of mechanisms. The charge carriers may drift to the electrodes of one of the diodes under an electric field. The field may be an external electric field. The electrical contact 119B may include discrete portions each of which is in electrical contact with the discrete regions 114.

Figure 1C:
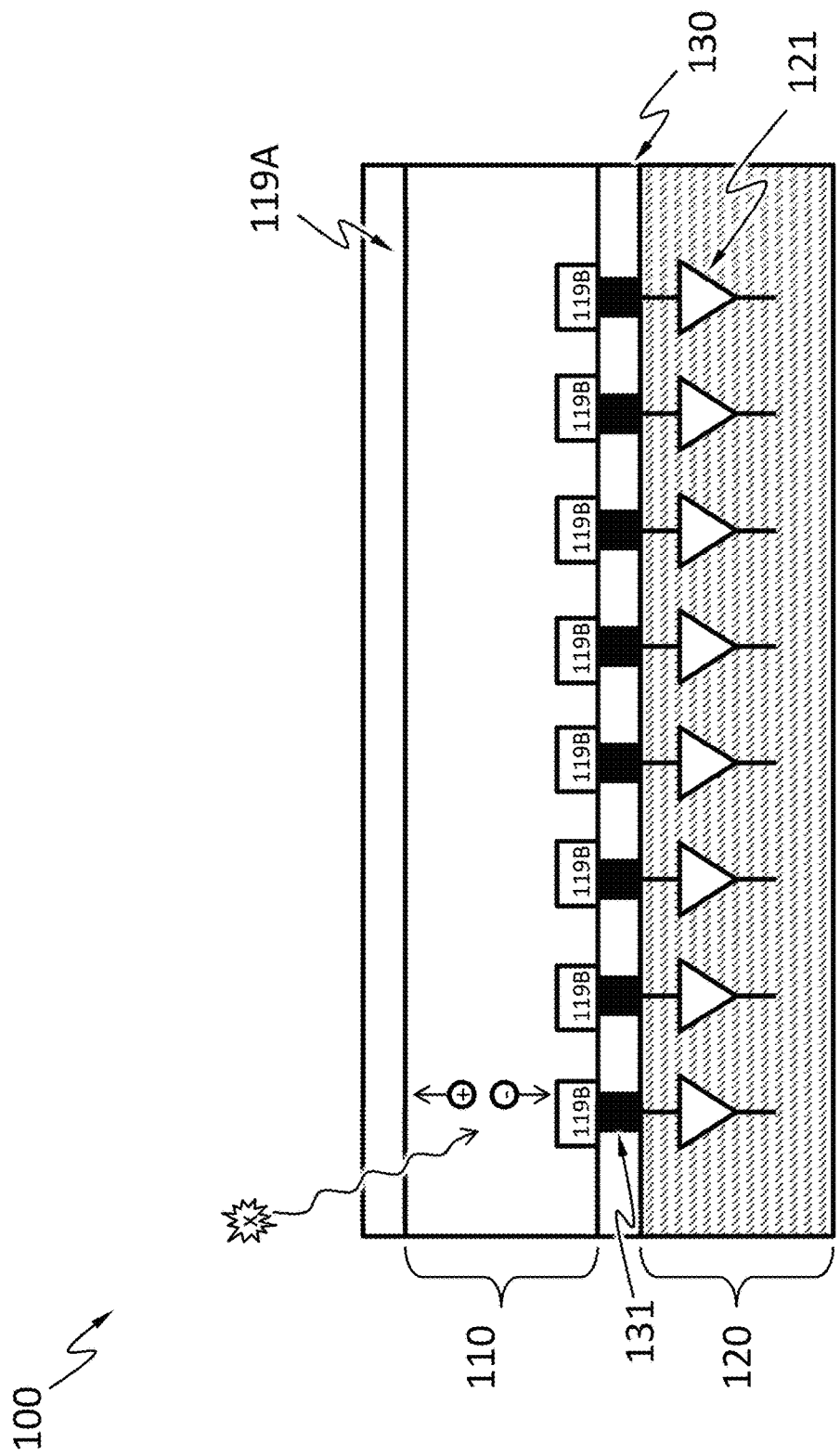
FIG. 1C schematically shows an alternative detailed cross-sectional view of the detector, according to an embodiment of the present teaching.

As shown in an alternative detailed cross-sectional view of the detector 100 in FIG. 1C, according to an embodiment, the X-ray absorption layer 110 may include a resistor of a semiconductor material such as, silicon, germanium, GaAs, CdTe, CdZnTe, or a combination thereof, but does not include a diode.

When an X-ray photon hits the X-ray absorption layer 110 including a resistor but not diodes, it may be absorbed and generate one or more charge carriers by a number of mechanisms. The charge carriers may drift to the electrical contacts 119A and 119B under an electric field. The electrical contact 119B includes discrete portions.

The electronics layer 120 may include an electronics system 121 configured to process or interpret signals generated by X-ray photons incident on the X-ray absorption layer 110. The electronics system 121 may include an analog circuitry such as a filter network, amplifiers, integrators, and comparators, or a digital circuitry such as a microprocessors, and memory. The electronics system 121 may include components shared by the pixels or components dedicated to a single pixel. For example, the electronics system 121 may include an amplifier dedicated to each pixel and a microprocessor shared among all the pixels. The electronics system 121 may be electrically connected to the pixels by vias 131. Space among the vias 131 may be filled with a filler material 130, which may increase the mechanical stability of the connection of the electronics layer 120 to the X-ray absorption layer 110. Other bonding techniques are possible to connect the electronics system 121 to the pixels without using vias.

Figure 1D:
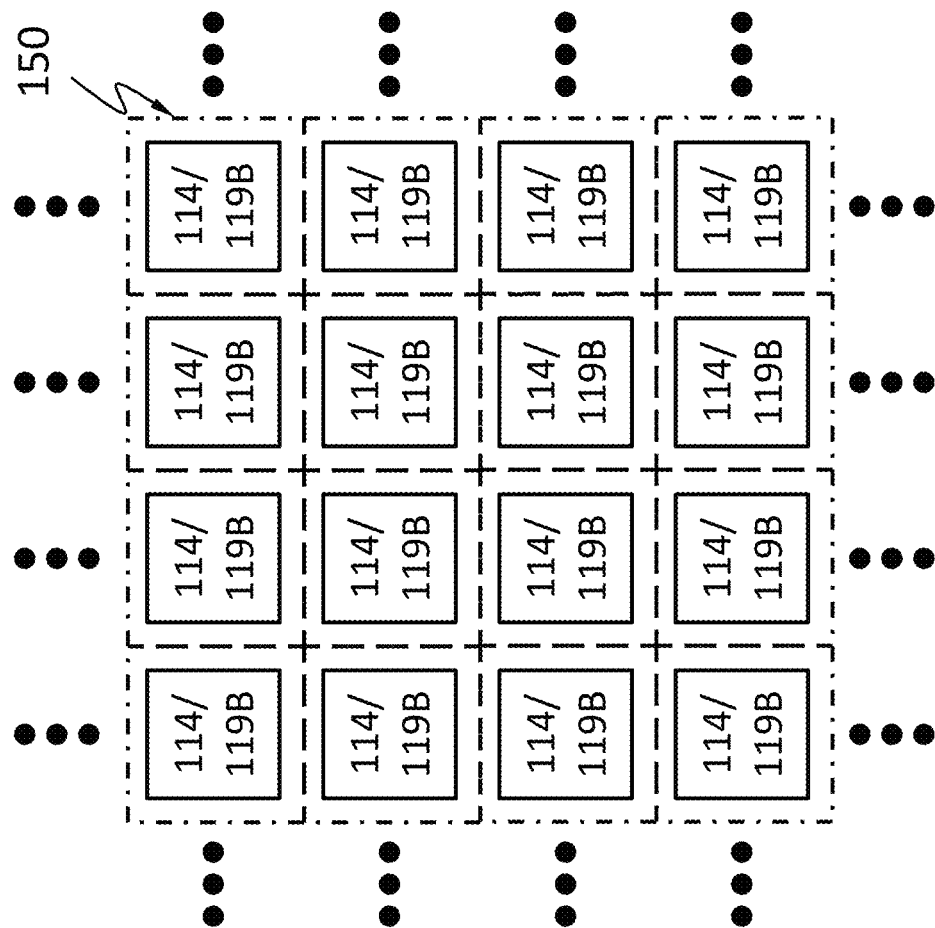
FIG. 1D shows an exemplary top view of a portion of the detector, according to an embodiment of the present teaching.

FIG. 1D shows an exemplary top view of a portion of the semiconductor X-ray detector 100 with a 4-by-4 array of discrete regions 114/119B. Charge carriers generated by an X-ray photon incident around the footprint of one of these discrete regions 114/119B are not substantially shared with another of these discrete regions 114/119B. The area 150 around a discrete region 114/119B in which substantially all (more than 95%, more than 98% or more than 99% of) charge carriers generated by an X-ray photon incident therein flow to the discrete region 114/119B is called a pixel associated with that discrete region 114/119B. Namely, less than 5%, less than 2% or less than 1% of these charge carriers flow beyond the pixel, when the X-ray photon hits inside the pixel. By measuring the rate of change of the voltage of each of the discrete regions 114/119B, the number of X-ray photons absorbed (which relates to the incident X-ray intensity) and/or the energies thereof in the pixels associated with the discrete regions 114/119B may be determined. Thus, the spatial distribution (e.g., an image) of incident X-ray intensity may be determined by individually measuring the rate of change of the voltage of each one of an array of discrete regions 114/119B. The pixels may be organized in any suitable array, such as, a square array, a triangular array and a honeycomb array. The pixels may have any suitable shape, such as, circular, triangular, square, rectangular, and hexangular. The pixels may be individually addressable.

Figure 2A:
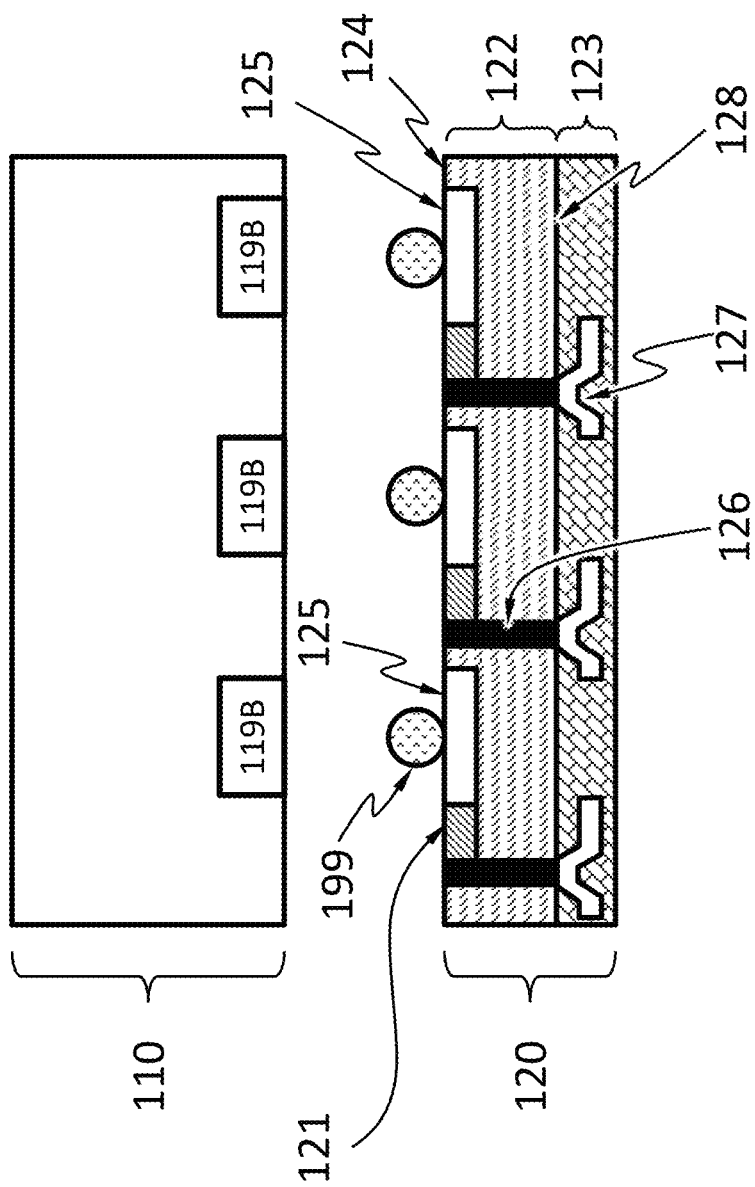
FIG. 2A schematically shows the electronics layer.

FIG. 2A schematically shows the electronics layer 120 according to an embodiment. The electronics layer 120 comprises a substrate 122 having a first surface 124 and a second surface 128. A "surface" as used herein is not necessarily exposed, but can be buried wholly or partially. The electronics layer 120 comprises one or more electric contacts 125 on the first surface 124. The one or more electric contacts 125 may be configured to be electrically connected to one or more electrical contacts 119B of the X-ray absorption layer 110. The electronics system 121 may be in or on the substrate 122. The electronics layer 120 comprises one or more vias 126 extending from the first surface 124 to the second surface 128. The electronics layer 120 may comprise a redistribution layer (RDL) 123 on the second surface 128. The RDL 123 may comprise one or more transmission lines 127. The electronics system 121 is electrically connected to the electric contacts 125 and the transmission lines 127 through the vias 126.

The substrate 122 may be a thinned substrate. For example, the substrate may have at thickness of 750 microns or less, 200 microns or less, 100 microns or less, 50 microns or less, 20 microns or less, or 5 microns or less. The substrate 122 may be a silicon substrate or a substrate or other suitable semiconductor or insulator. The substrate 122 may be produced by grinding a thicker substrate to a desired thickness.

The one or more electric contacts 125 may be a layer of metal or doped semiconductor. For example, the electric contacts 125 may be gold, copper, platinum, palladium, doped silicon, etc.

The vias 126 pass through the substrate 122 and electrically connect electrical components (e.g., the electrical contacts 125) on the first surface 124 to electrical components (e.g., the RDL) on the second surface 128. The vias 126 are sometimes referred to as "through-silicon vias" although they may be fabricated in substrates of materials other than silicon.

The RDL 123 may comprise one or more transmission lines 127. The transmission lines 127 electrically connect electrical components (e.g., the vias 126) in the substrate 122 to bonding pads at other locations on the substrate 122. The transmission lines 127 may be electrically isolated from the substrate 122 except at certain vias 126 and certain bonding pads. The transmission lines 127 may be a material (e.g., Al) with small mass attenuation coefficient for the X-ray energy of interest. The RDL 123 may redistribute electrical connections to more convenient locations. The RDL 123 is especially useful when the detector 100 has a large number of pixels. If the detector 100 does not have a large number of pixels, the RDL 123 may be omitted and signals from the pixels may be routed on the first surface 124.

FIG. 2A further schematically shows bonding between the X-ray absorption layer 110 and the electronics layer 120 at the electrical contact 119B and the electrical contacts 125. The bonding may be by a suitable technique such as direct bonding or flip chip bonding.

Direct bonding is a wafer bonding process without any additional intermediate layers (e.g., solder bumps). The bonding process is based on chemical bonds between two surfaces. Direct bonding may be at elevated temperature but not necessarily so.

Flip chip bonding uses solder bumps 199 deposited onto contact pads (e.g., the electrical contact 119B of the X-ray absorption layer 110 or the electrical contacts 125). Either the X-ray absorption layer 110 or the electronics layer 120 is flipped over and the electrical contacts 119B of the X-ray absorption layer 110 are aligned to the electrical contacts 125. The solder bumps 199 may be melted to solder the electrical contact 119B and the electrical contacts 125 together. Any void space among the solder bumps 199 may be filled with an insulating material.

Figure 2B:
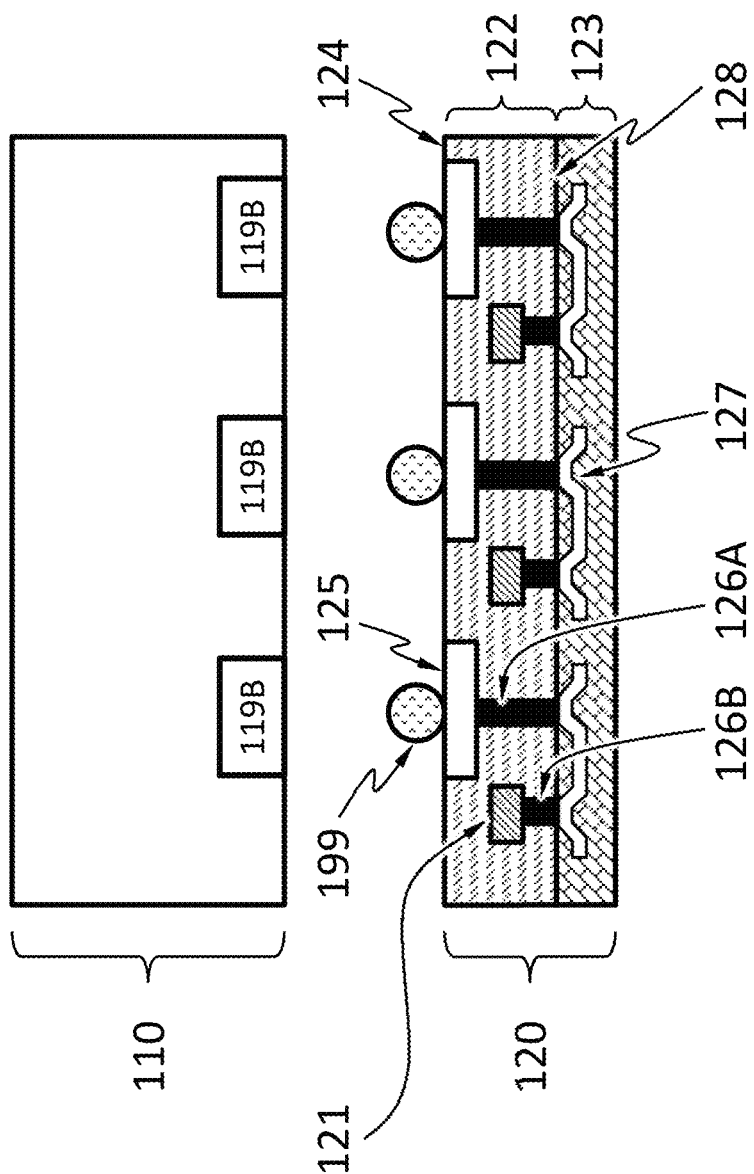
FIG. 2B schematically shows the electronics layer.

FIG. 2B schematically shows the electronics layer 120 according to an embodiment. The electronics layer 120 shown in FIG. 2B is different from the electronics layer 120 shown in FIG. 2A in the following ways. The electronics system 121 is buried in the substrate 122. The electronics layer 120 comprises one or more vias 126A extending from the first surface 124 to the second surface 128. The vias 126A electrically connect the electrical contacts 125 to the transmission lines 127 in the RDL 123 on the second surface 128. The electronics layer 120 further comprises one or more vias 126B extending from the second surface 128 to the electronics system 121. The vias 126B electrically connect the transmission lines 127 to the electronics system 121. The X-ray absorption layer 110 and the electronics layer 120 may also be bonded together (e.g., at the electrical contact 119B and the electrical contacts 125) by a suitable technique such as direct bonding or flip chip bonding.

Figure 2C:
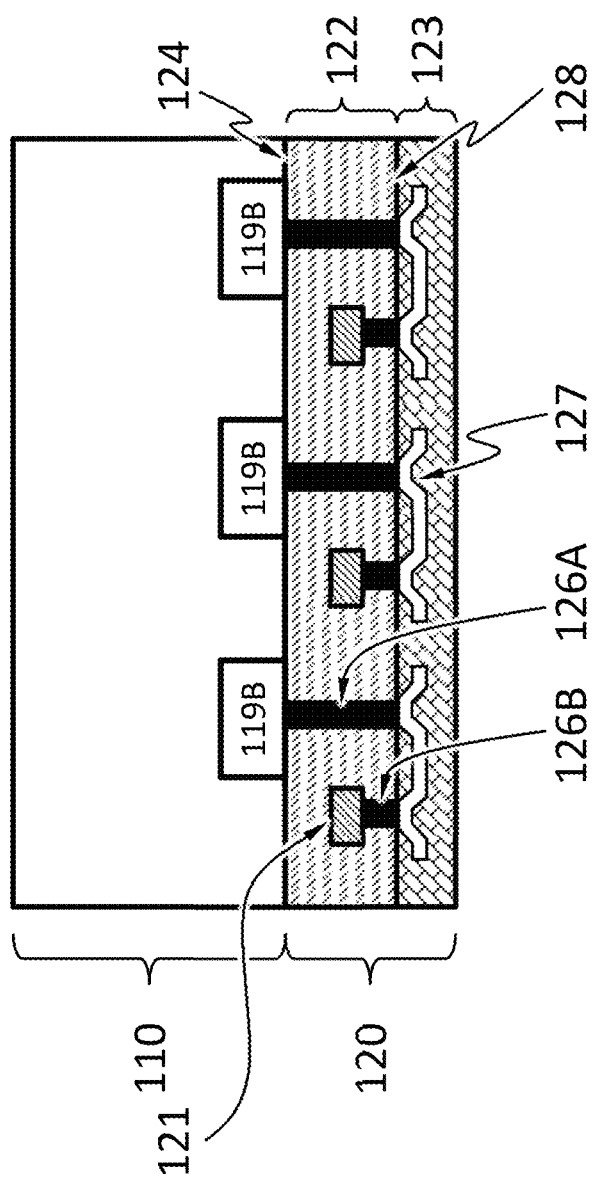
FIG. 2C schematically shows the electronics layer.

FIG. 2C schematically shows the electronics layer 120 according to an embodiment. The electronics layer 120 shown in FIG. 2C is different from the electronics layer 120 shown in FIG. 2A in the following ways. The electronics system 121 is buried in the substrate 122. The electronics layer 120 does not comprise one or more electric contacts 125 on the first surface 124. Instead, the substrate 122 including the buried electronics system 121 is bonded to the X-ray absorption layer 110 by direct bonding. Holes are formed in the substrate 123 and filled with metal to form the vias 126A that electrically route the electrical contact 119B to the second surface 128 and to form the vias 126B that electrically route the electronics system 121 to the second surface 128. The RDL 123 is then formed on the second surface 128 such that the transmission lines 127 electrically connect the vias 126A and 126B to complete the electrical connection from the electrical contact 119B to the electronics system 121.

The X-ray absorption layer 110 may include multiple discrete chips. Each of the chips may be bonded to the electronics layer 120 individually or collectively. The X-ray absorption layer 110 including multiple discrete chips may help to accommodate the difference between the coefficients of thermal expansion of the materials of the X-ray absorption layer 110 and the electronics layer 120. The coefficients of thermal expansion may be coefficients of linear thermal expansion or volumetric thermal expansion.

The X-ray absorption layer 110 may be a different material from the substrate 122 of the electronics layer 120. For example, the X-ray absorption layer 110 may be GaAs and the substrate 122 may be silicon. Bonding of the X-ray absorption layer 110 and the electronics layer 120 usually occurs at an elevated temperature and the X-ray absorption layer 110 and the electronics layer 120 are cooled to the room temperature after bonding. The X-ray absorption layer 110 and the electronics layer 120 are usually at the same temperature at any given moment during the bonding process. The X-ray absorption layer 110 and the electronics layer 120 are usually heated and cooled together. When the X-ray absorption layer 110 and the substrate 122 of the electronics layer 120 have substantially different coefficients of thermal expansion, cooling the X-ray absorption layer 110 and the electronics layer 120 from the same elevated temperature to the room temperature causes significant stress at the interface between the X-ray absorption layer 110 and the electronics layer 120. The stress may cause failure in the detector 100.

FIG. 3A schematically shows thermal expansion of the X-ray absorption layer 110 and the electronics layer 120 during the bonding process if the X-ray absorption layer 110 and the substrate 122 of the electronics layer 120 have substantially different coefficients of thermal expansion and the X-ray absorption layer 110 and the electronics layer 120 are always at the same temperature at any given moment during the bonding process. The initial temperature of the X-ray absorption layer 110 and the electronics layer 120 is T1. The X-ray absorption layer 110 and the electronics layer 120 are then heated to T2. As FIG. 3A schematically shows, the X-ray absorption layer 110 expands more than the substrate 122 of the electronics layer 120 does because the X-ray absorption layer 110 has a higher coefficient of thermal expansion than the substrate 122. The X-ray absorption layer 110 and the electronics layer 120 are further heated to T3. At T3, the difference of the expansion of the X-ray absorption layer 110 and the expansion of the electronics layer 120 is even more pronounced than at T2. The X-ray absorption layer 110 and the electronics layer 120 are bonded at T3, while they are in their respective but different expanded states. The bonded X-ray absorption layer 110 and electronics layer 120 are then cooled from T3 to T2. Because the X-ray absorption layer 110 and the electronics layer 120 are now bonded, neither can contract to their respective sizes at T2 before bonding. A compressive stress and a tensile stress respectively develop in the X-ray absorption layer 110 and the substrate 122. As the bonded X-ray absorption layer 110 and electronics layer 120 are further cooled from T2 to T1, the compressive stress and the tensile stress respectively in the X-ray absorption layer 110 and the substrate 122 increase. The stress may not be uniform across the entire interface between the X-ray absorption layer 110 and the electronics layer 120.

Figure 3B:
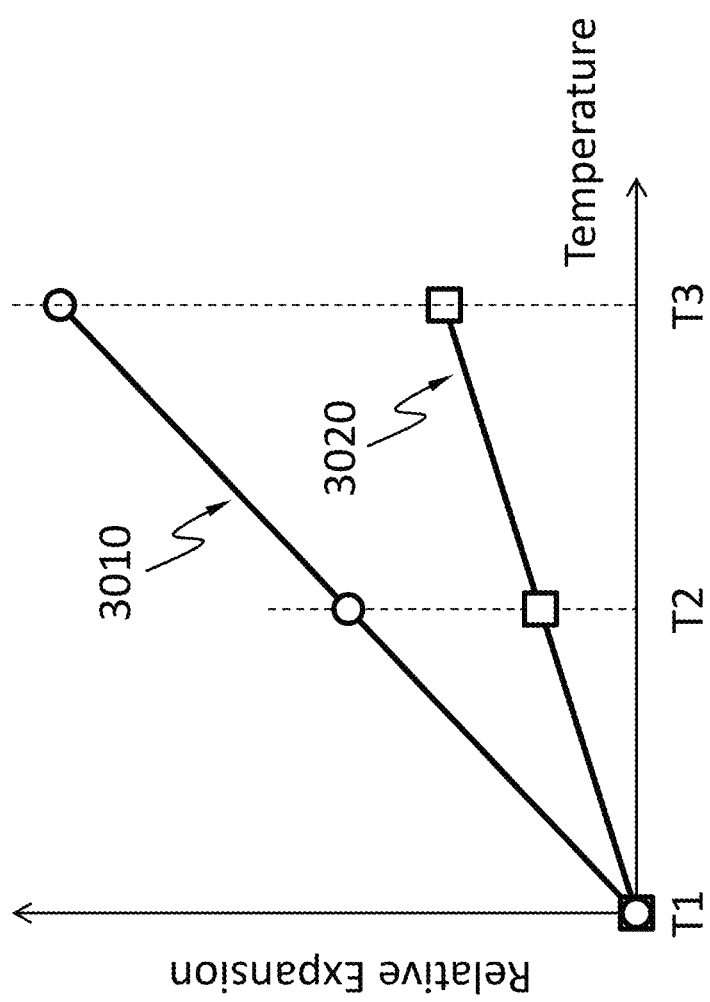
FIG. 3B shows plots of the relative thermal expansion as a function of temperature of the X-ray absorption layer and the substrate of the electronics layer, respectively, before the X-ray absorption layer and the electronics layer are bonded.

As shown in FIG. 3B, the lines 3010 and 3020 are the plots of the relative thermal expansion as a function of temperature of the X-ray absorption layer 110 and the substrate 122 of the electronics layer 120, respectively, before the X-ray absorption layer 110 and the electronics layer 120 are bonded. The slopes of the lines 3010 and 3020 are the coefficients of thermal expansion for the X-ray absorption layer 110 and the substrate 122 of the electronics layer 120, respectively. The line 3010 has a higher slope than the line 3020, which means that the X-ray absorption layer 110 has a greater coefficient of thermal expansion than the substrate 122. At T2 or T3, the relative thermal expansion of the X-ray absorption layer 110 is greater than the relative thermal expansion of the substrate 122.

Figure 4A:
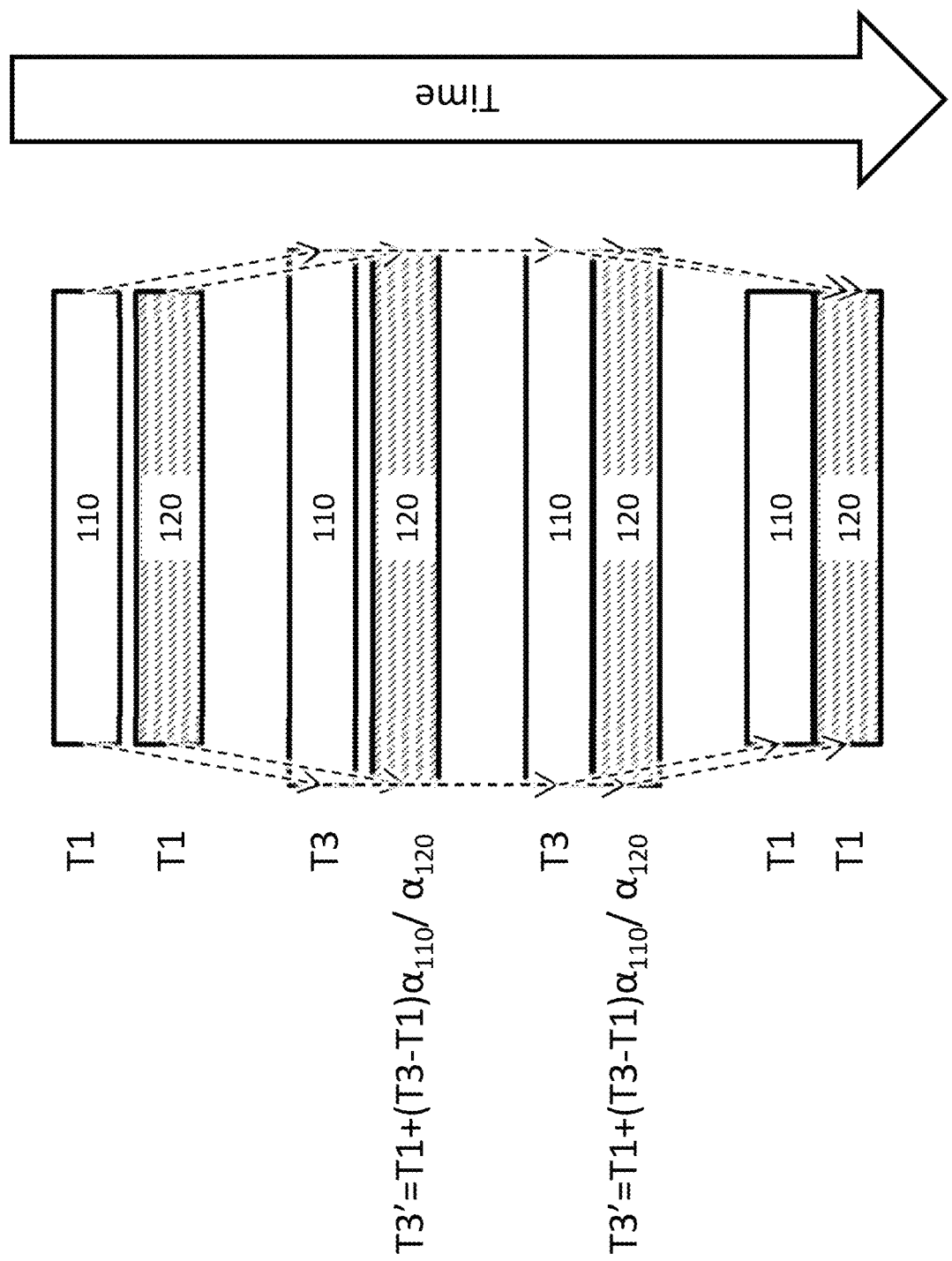
FIG. 4A schematically shows thermal expansion of the X-ray absorption layer and the electronics layer during the bonding process if the X-ray absorption layer and the substrate of the electronics layer have substantially different coefficients of thermal expansion and the temperatures of the X-ray absorption layer and the electronics layer are separately controlled during the bonding process.

FIG. 4A schematically shows thermal expansion of the X-ray absorption layer 110 and the electronics layer 120 during the bonding process if the X-ray absorption layer 110 and the substrate 122 of the electronics layer 120 have substantially different coefficients of thermal expansion and the temperatures of the X-ray absorption layer 110 and the electronics layer 120 are separately controlled during the bonding process. The initial temperature of the X-ray absorption layer 110 and the electronics layer 120 is T1. The X-ray absorption layer 110 is heated to T3 and the electronics layer 120 heated to T3'. The X-ray absorption layer 110 and the electronics layer 120 are not necessarily heated at the same time. For example, the X-ray absorption layer 110 may be heated to T3 while the electronics layer 120 is still at T1, and the electronics layer 120 may be heated to T3' while the X-ray absorption layer 110 is held at T3. The X-ray absorption layer 110 at T3 has the same relative thermal expansion as the electronics layer 120 at T3'. In an example, T3'=T1+ (T3−T1)$\alpha_{110}/\alpha_{120}$, where $\alpha_{110}$ is the coefficient of linear thermal expansion of the X-ray absorption layer 110 and $\alpha_{120}$ is the coefficient of linear thermal expansion of the substrate 122 of the electronics layer 120. The coefficient of linear thermal expansion a of an object is defined as $$\alpha = \frac{1}{L}\frac{dL}{dT}$$

where L is a linear dimension of the object. The X-ray absorption layer 110 and the electronics layer 120 are bonded when the X-ray absorption layer 110 is at T3 and the electronics layer 120 is at T3'. The bonded X-ray absorption layer 110 and electronics layer 120 are then cooled from respectively from T3 to T1 and from T3' to T1. During the cooling process, the temperatures of the X-ray absorption layer 110 and the electronics layer 120 are controlled such that their relative thermal expansions are essentially the same (i.e., <10% difference). As a result, there is essentially no stress caused by the difference in the coefficients of thermal expansion at the interface of the X-ray absorption layer 110 and the substrate 122 of the electronics layer 120.

As shown in FIG. 4B, the lines 4010 and 4020 are the plots of the relative thermal expansion as a function of temperature of the X-ray absorption layer 110 and the substrate 122 of the electronics layer 120, respectively, before the X-ray absorption layer 110 and the electronics layer 120 are bonded. The slopes of the lines 4010 and 4020 are the coefficients of thermal expansion for the X-ray absorption layer 110 and the substrate 122 of the electronics layer 120, respectively. The line 4010 has a higher slope than the line 4020, which means that the X-ray absorption layer 110 has a greater coefficient of thermal expansion than the substrate 122. When the X-ray absorption layer 110 and the electronics layer 120 are respectively at T3 and T3', the relative thermal expansion of the X-ray absorption layer 110 is equal to the relative thermal expansion of the substrate 122.

Figure 5:
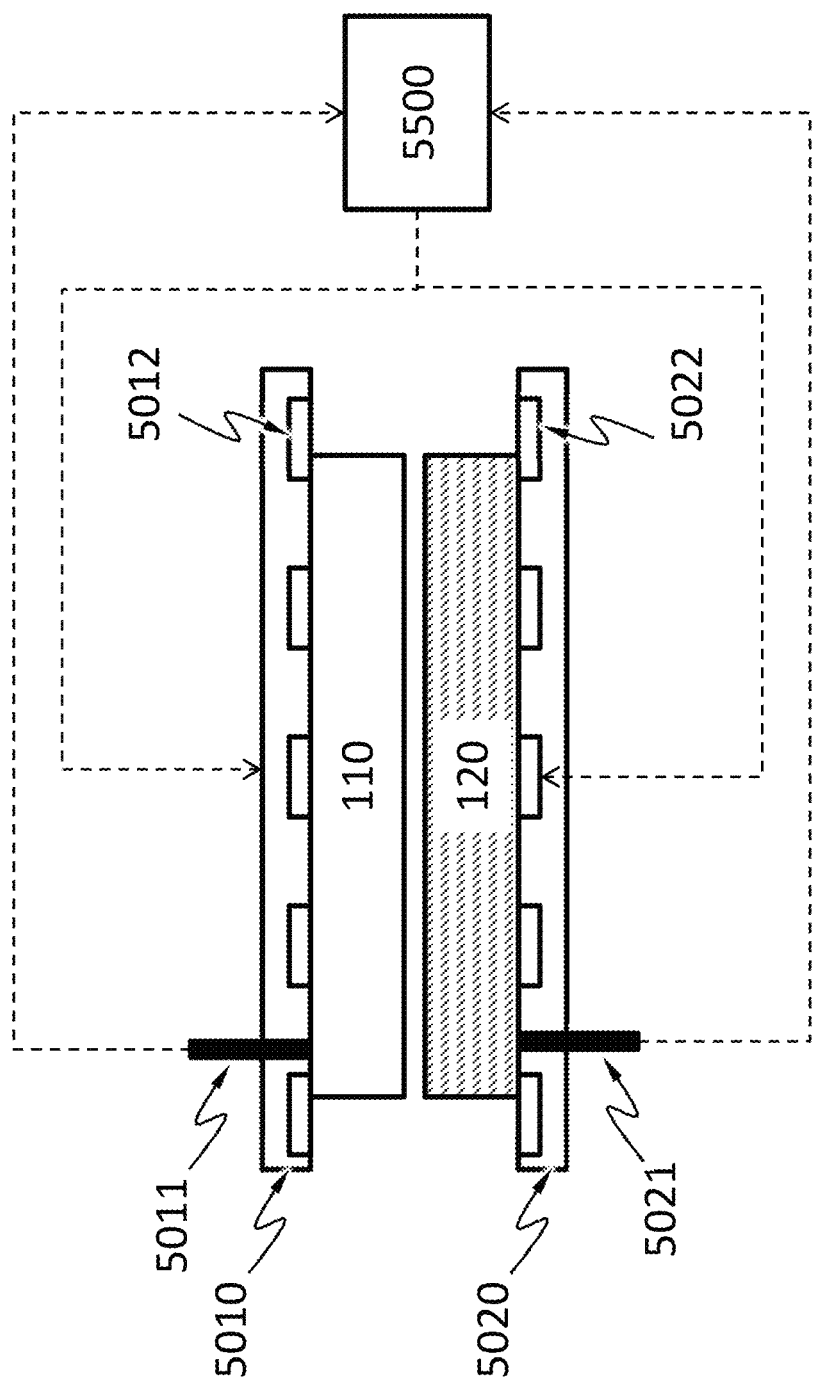
FIG. 5 schematically shows an upper chuck and a lower chuck of a wafer bonding system.

A wafer bonding system usually sandwiches two wafers (or a wafer and multiple chips) to be bonded between two chucks. FIG. 5 schematically shows an upper chuck 5010 and a lower chuck 5020 of a wafer bonding system, and the X-ray absorption layer 110 and the electronics layer 120 positioned between the upper chuck 5010 and the lower chuck 5020. A gap is shown between the X-ray absorption layer 110 and the electronics layer 120 to indicate that the X-ray absorption layer 110 and the electronics layer 120 have not been bonded. The chucks 5010 and 5020 may respectively include temperature drivers (e.g., heaters or coolers) 5012 and 5022 therein. The temperature drivers are configured to change the temperatures of the chucks 5010 and 5020, respectively. The wafer bonding system may have temperature sensors 5011 and 5021 configured to measure the temperatures of the X-ray absorption layer 110 and the electronics layer 120. The temperature drivers 5012 and 5022 in the chucks 5010 and 5020 may be controlled by a controller 5500 based on the temperatures of the X-ray absorption layer 110 and the electronics layer 120 obtained by the temperature sensors 5011 and 5021. The controller 5500 may include a processor and a memory. The memory is configured to have programs stored therein. The processor is configured to control the powers of the temperature drivers 5012 and 5022 by executing a program in the memory. For example, a program may cause the processor to set the powers to the powers of the temperature drivers 5012 and 5022 such that the relative thermal expansions of the X-ray absorption layer 110 and the electronics layer 120 are essentially the same (i.e., <10% difference) at all time during a bonding process.

FIG. 6 schematically shows a flow of a method of bonding a layer of a first material and a layer of a second material, where the first and second materials have dissimilar coefficients of thermal expansion. For example, the first layer may be the X-ray absorption layer 110 and the second layer may be the electronics layer 120 of the X-ray detector 100. In procedure 6010, the layer of the first material (e.g., the X-ray absorption layer 110) is set to a first temperature and the layer of the second material (e.g., the electronics layer 120) is set to a second temperature. In procedure 6020, the layer of the first material and the layer of the second material are bonded while the layer of the first material is at the first temperature and the layer of the second material is at the second temperature. The layer of the first material and the layer of the second material may be bonded by a suitable technique such as direct bonding or flip chip bonding. Solder bumps or balls may be but not necessarily used. In procedure 6030, the temperatures of the layer of the first material and the layer of the second material are changed toward a third temperature while maintaining the relative thermal expansions of these layers essentially equal (i.e., <10% difference) at all time before the temperatures of the layer of the first material and the layer of the second material reach the third temperature. Changing the temperatures of the layer of the first material and the layer of the second material includes using a temperature driver in the layer of the first material or in the layer of the second material. The third temperature may be the room temperature. The third temperature may be a temperature below 40° C. The relative thermal expansions in this flow are relative to the dimensions of the layer of the first material and the layer of the second material at the third temperature, respectively.

Figure 7A:
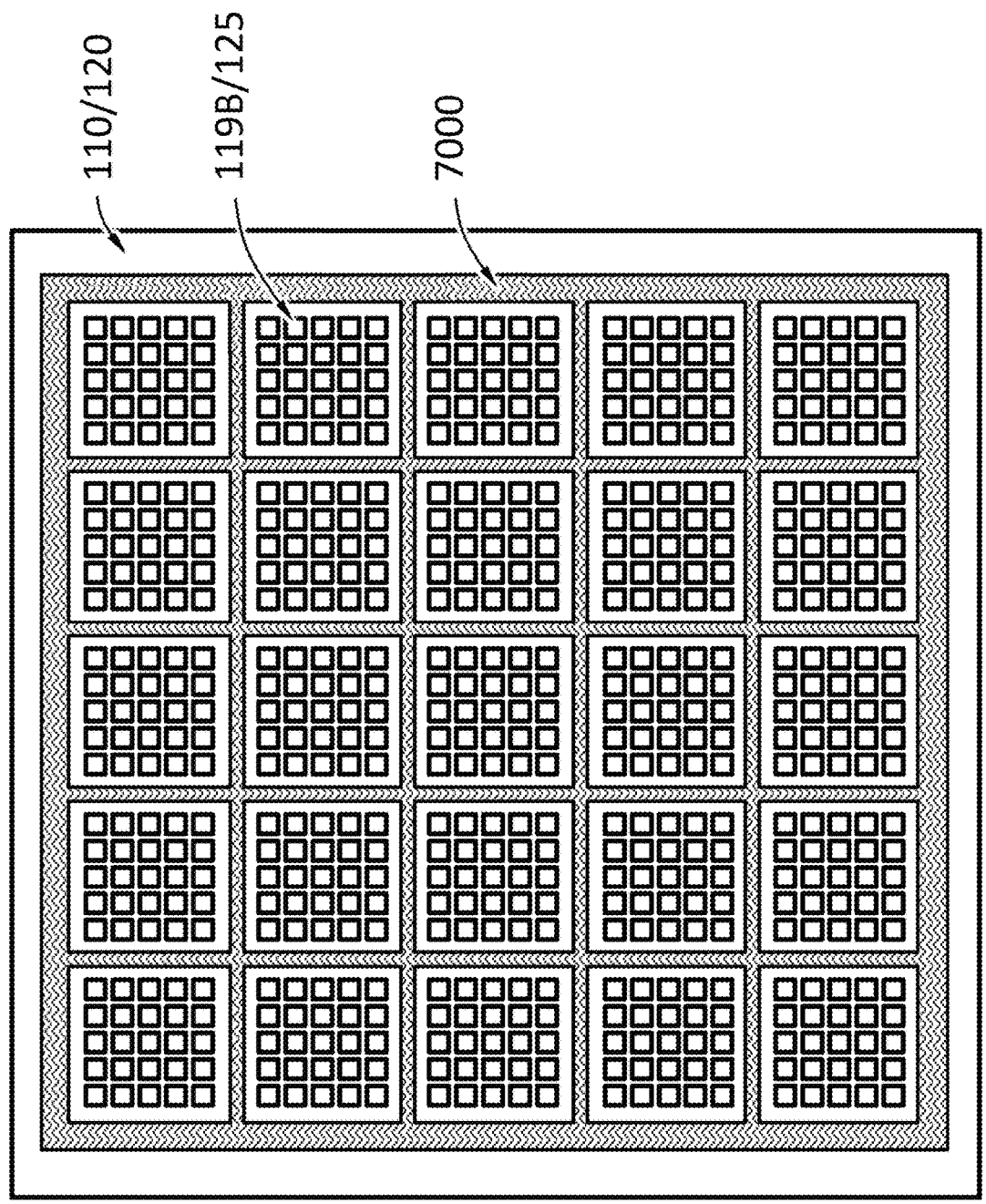
FIG. 7A schematically shows that the X-ray absorption layer or the electronics layer may include a temperature driver therein.

FIG. 7A schematically shows that the X-ray absorption layer 110 or the electronics layer 120 may include a temperature driver 7000 therein. The temperature drivers 7000 are configured to change the temperatures of the X-ray absorption layer 110 or the electronics layer 120, respectively. The temperature driver 7000 may be embedded in or on the surface of the X-ray absorption layer 110 or the electronics layer 120. The temperature driver 7000 may be a resistive heater or a Peltier device (which may heat or cool depending on the electric current direction through the Peltier device). The temperature driver 7000 may be arranged around, underneath or in between the electrical contacts 119B or the electrical contacts 125.

Figure 7B:
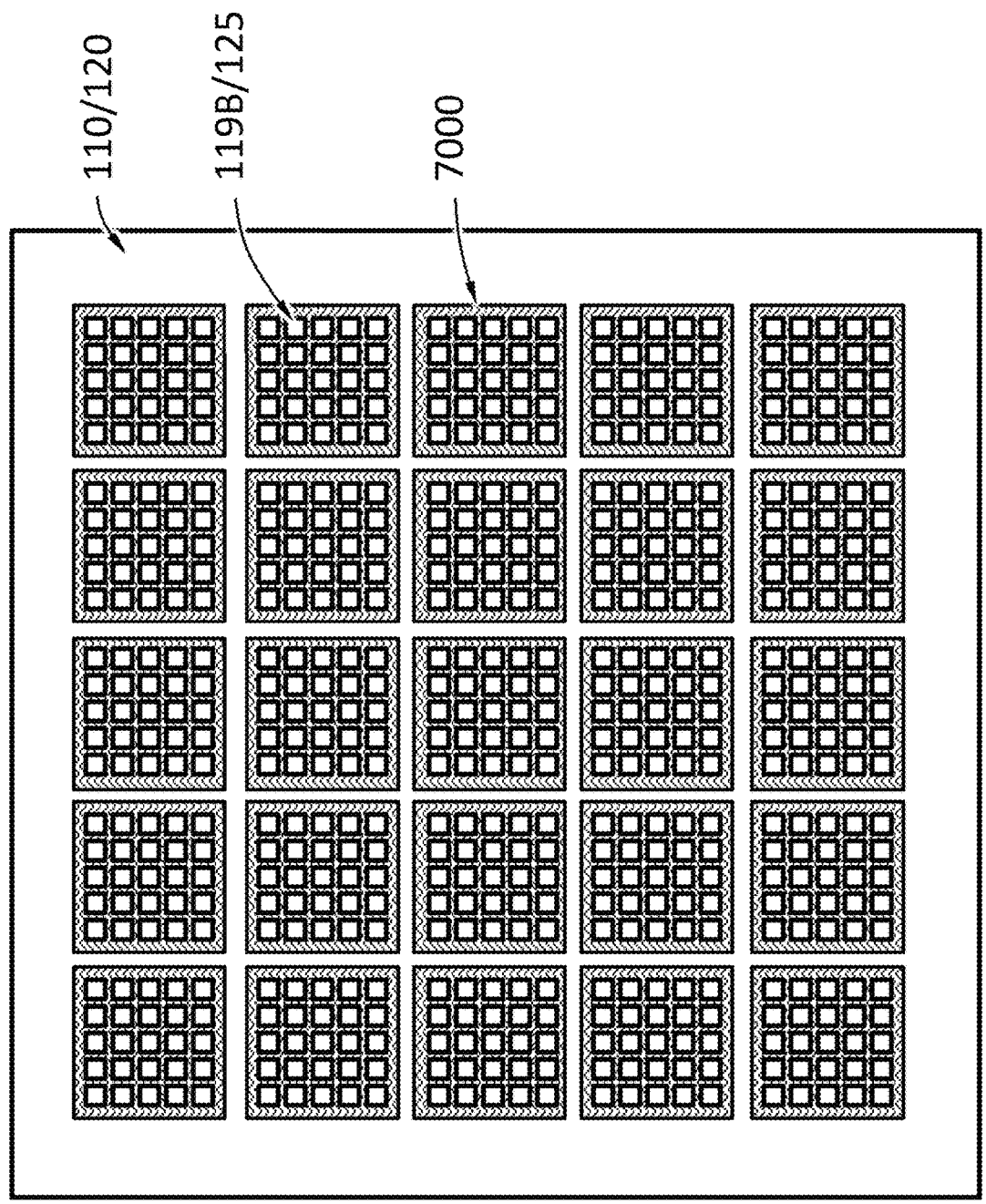
FIG. 7B schematically shows that the temperature driver in the X-ray absorption layer or the electronics layer may include multiple individually addressable units.

FIG. 7B schematically shows that the temperature driver 7000 may include multiple individually addressable units. These individually addressable units may be controlled independently from one another and may be used to locally heat or cool one or more areas of the X-ray absorption layer 110 or the electronics layer 120. The individually addressable units are useful to make the temperatures across the X-ray absorption layer 110 or the electronics layer 120 more uniform. The individually addressable units are especially useful when the X-ray absorption layer 110 or the electronics layer 120 include multiple discrete chips. In an example, the chips of one of the X-ray absorption layer 110 and the electronics layer 120 may not be positioned onto the other one of the X-ray absorption layer 110 and the electronics layer 120 at the same time. If a chip is positioned onto the other one of the X-ray absorption layer 110 and the electronics layer 120 without being bonded thereto before the next chip is positioned, the chip may shift and thus ruin the alignment of the chip. The individually addressable units can be used to locally heat the location to which the chip is positioned and thereby bond the chip before the next chip is positioned. When the X-ray absorption layer 110 includes multiple chips and uses a III-V semiconductor (e.g., GaAs) for absorption of X-ray and the substrate 122 of the electronics layer 120 is a silicon substrate, the chips may be bonded to the substrate 122 using solder bumps. Forming solder bumps on silicon is easier than forming solder bumps on III-V semiconductors. The individually addressable units may be used to melt the bumps at a location to which a chip is positioned before the next chip is positioned thereby bond the chip, while keeping solder bumps elsewhere below their melting point.

Figure 7C:
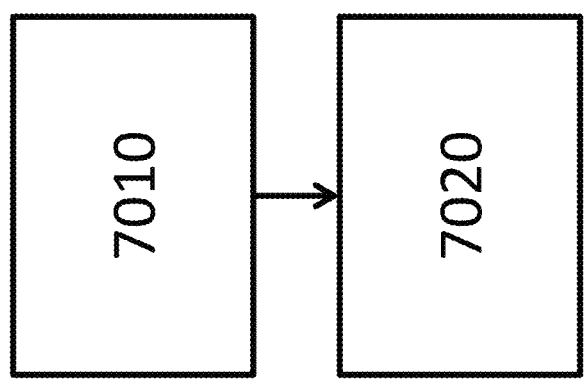
FIG. 7C schematically shows a flow for bonding a plurality of chips to a wafer having a temperature driver that includes multiple individually addressable units.

FIG. 7C schematically shows a flow for bonding a plurality of chips to a wafer having a temperature driver that includes multiple individually addressable units. In procedure 7010, one of the chips is positioned to a location of the wafer. In procedure 7020, that chip is bonded to the wafer by changing a temperature of the location using the individually addressable units, without changing a temperature of another location of the wafer using the individually addressable units. The chip may be bonded before another chip is positioned to the wafer. The chips may be part of the X-ray absorption layer 110 and the wafer may be part of the electronics layer 120. The chip may include a III-V semiconductor such as GaAs. The wafer may include silicon. There may be solder bumps between that chip positioned to the location and the wafer. There may be solder bumps elsewhere on the wafer. The temperature of the location may be changed using the individually addressable units such that the solder bumps at the location are melted during bonding. The solder at the location is then cooled and solidified. The solder at the location may remain solid while bonding occurs at other locations.

Figure 8A:
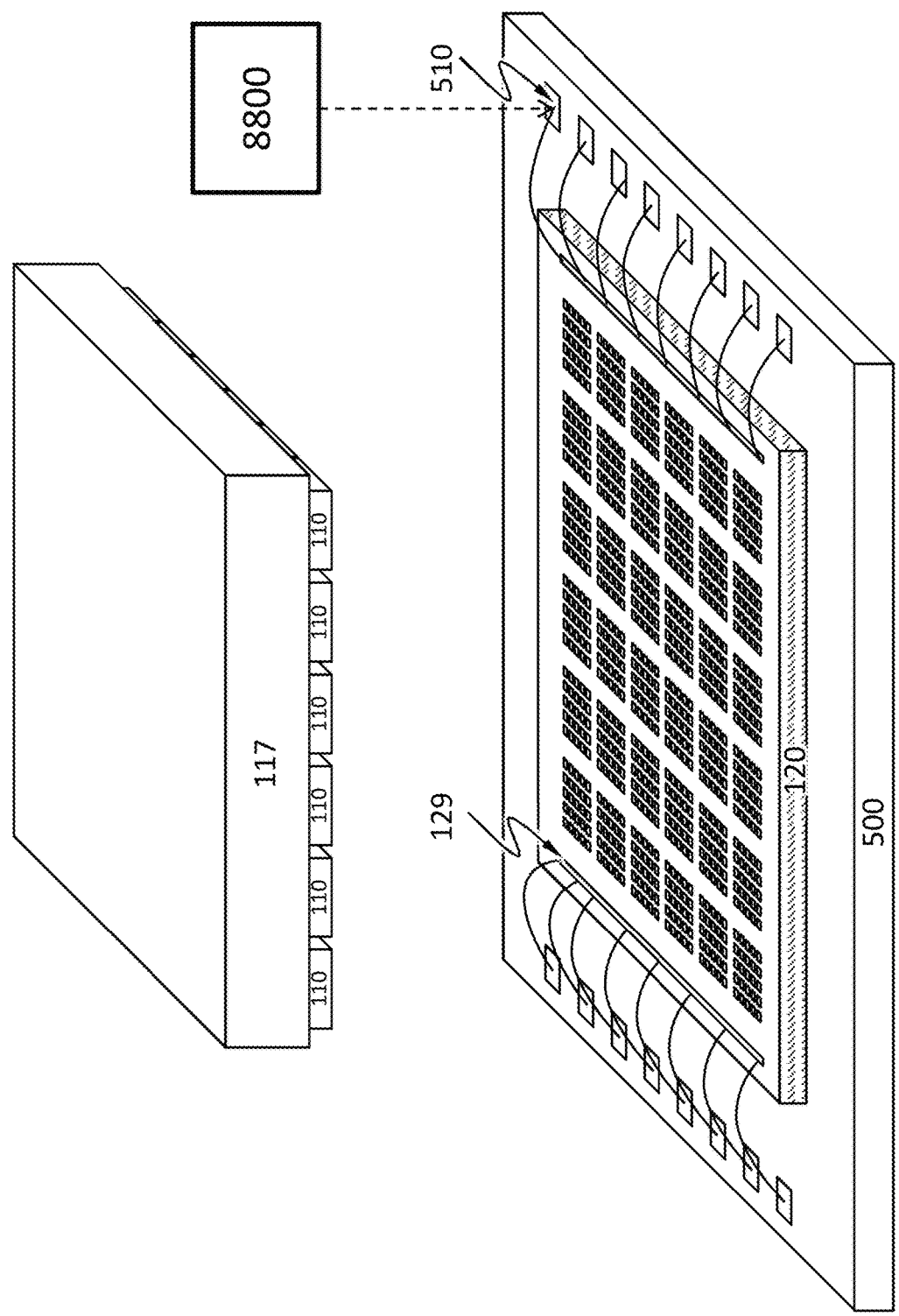
FIG. 8A schematically shows, as an example, that the electronics layer includes bonding pads electrically connected to the temperature driver in the electronics layer.
Figure 8B:
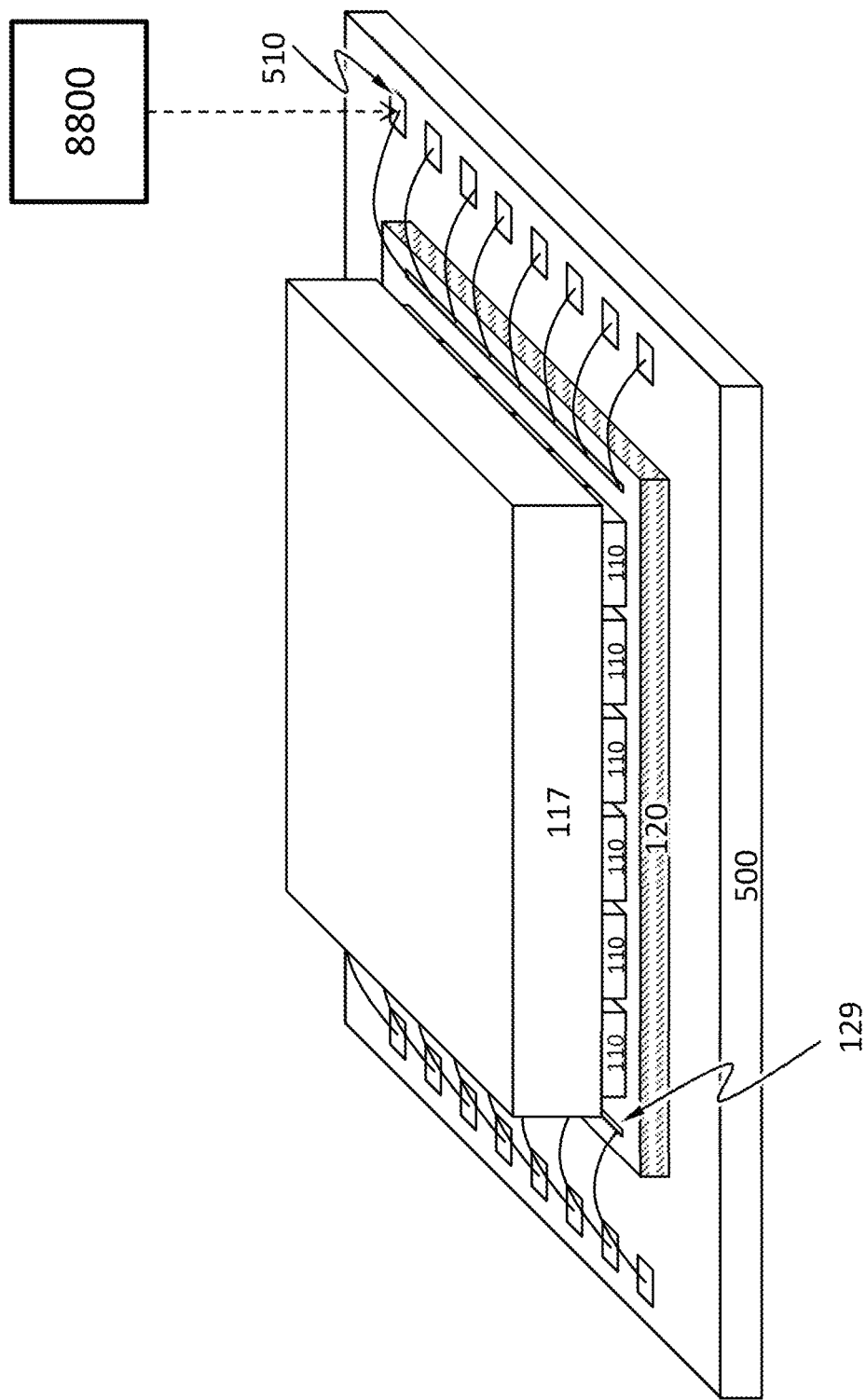
FIG. 8B shows that the X-ray absorption layer in FIG. 8A includes multiple chips.

As FIG. 8A schematically shows, as an example, that the electronics layer 120 includes bonding pads 129 electrically connected to the temperature driver 7000 in the electronics layer 120. The electronics layer 120 is mounted to a support 500. The bonding pads 129 and bonding pads 510 of the support 500 may be electrically connected by wire bonding. A controller 8800 in or outside the support 500 regulates the power supplied to the temperature driver 7000. FIG. 8B shows that the X-ray absorption layer 110 includes multiple chips. The chips may be supported on a carrier 117. The chips are mounted on to the electronics layer 120 such that the electrical contacts 119B and the electrical contacts 125 are aligned. The flow of FIG. 6 is applied to the X-ray absorption layer 110 and the electronics layer 120 where the temperature of the electronics layer 120 is controlled using the temperature driver 7000 in the electronics layer 120. If the temperature driver 7000 in the electronics layer 120 includes multiple individually addressable units, bonding of the electronics layer 120 and the different chips of the X-ray absorption layer 110 may occur at different time. For example, some of the chips may be mounted to and bonded to the electronics layer 120 before others of the chips are mounted to and bonded to the electronics layer 120. The temperature of the X-ray absorption layer 110 may be controlled using an external temperature driver or any temperature driver 7000 in the X-ray absorption layer 110. For example, the temperature of the X-ray absorption layer 110 may be controlled using a temperature driver in the carrier 117 or in a chuck. The system of FIG. 8A and FIG. 8B are also applicable to the situation where the electronics layer 120 includes multiple chips.

Figure 9:
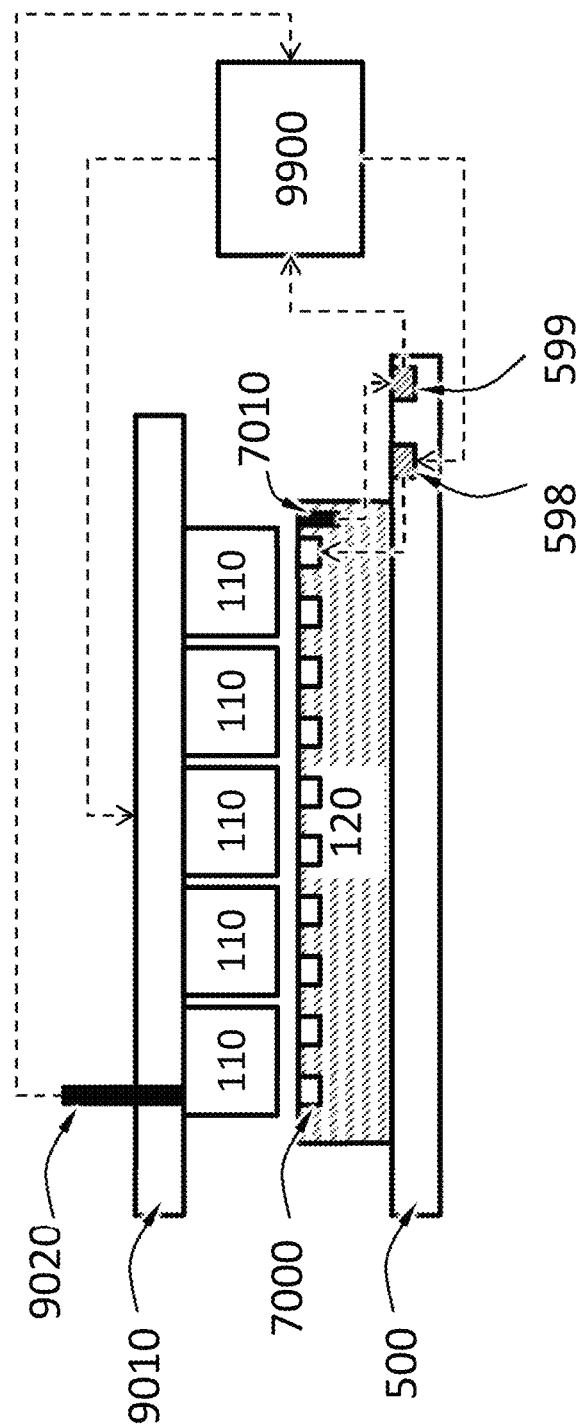
FIG. 9 schematically shows a wafer bonding system configured to power and control the temperature drivers in the X-ray absorption layer or in the in the electronics layer.

FIG. 9 schematically shows a wafer bonding system configured to power and control the temperature drivers 7000 in a first layer such as the X-ray absorption layer 110 or in a second layer such as the in the electronics layer 120. FIG. 9 shows an example where the system powers and controls the temperature drivers 7000 in the second layer such as the electronics layer 120 but the system can equally power and control the temperature drivers 7000 in the first layer such as the X-ray absorption layer 110. The first layer such as the X-ray absorption layer 110 may have multiple chips. The first layer may be thermally connected to a temperature driver 9010 and the temperature of the first layer may be measured by a temperature sensor 9020. In this example, the second layer such as the electronics layer 120 has the temperature drivers 7000 therein. The second layer such as the electronics layer 120 may have a temperature sensor 7010 therein or the system may have a temperature 7010 outside the second layer. The chips of the first layer are positioned on the second layer. A gap is shown between the first layer and the second layer to indicate that they have not been bonded. The second layer may be mounted to the support 500, which has an electrical contact 598 that is electrically connected to the temperature driver 7000 in the electronics layer 120, and an electrical contact 599 electrically connected to the temperature sensor 7010 if the temperature sensor 7010 is in the second layer. The temperature drivers 7000 and 9010 may be controlled by a controller 9900 based on the temperatures of the first and second layers obtained by the temperature sensors 9020 and 7010. The controller 9900 may include a processor and a memory. The memory is configured to have programs stored therein. The processor is configured to control the powers of the temperature drivers 7000 and 9010 by executing a program in the memory. For example, a program, when executed, may cause the processor to set the powers to the temperature drivers 7000 and 9010 such that the relative thermal expansions of the first and second layers are essentially the same (i.e., <10% difference) at all time during a bonding process.

Figure 10A:
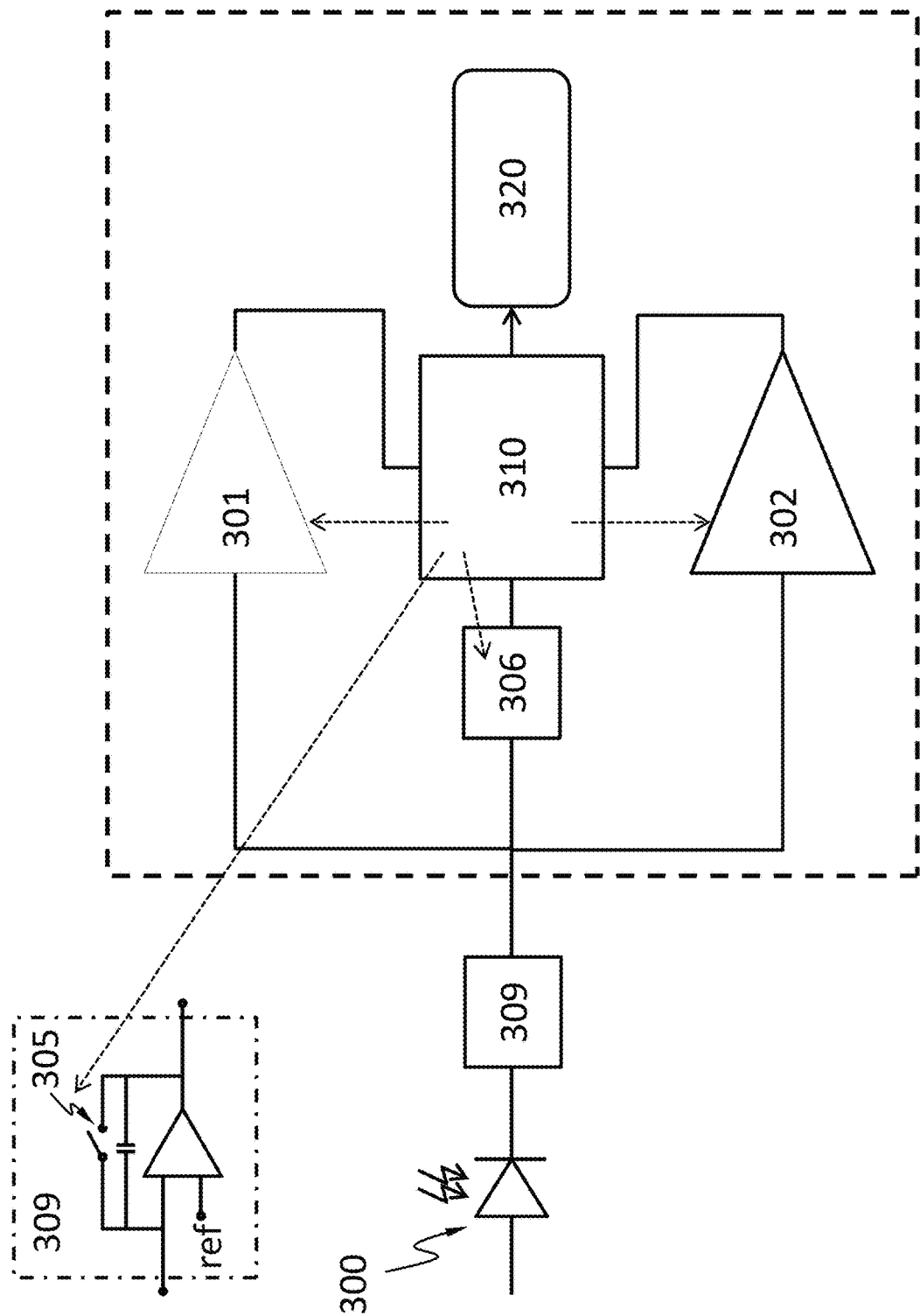
FIG. 10A and FIG. 10B each show a component diagram of an electronics system of the detector in FIG. 1A, FIG. 1B or FIG. 1C, according to an embodiment.
Figure 10B:
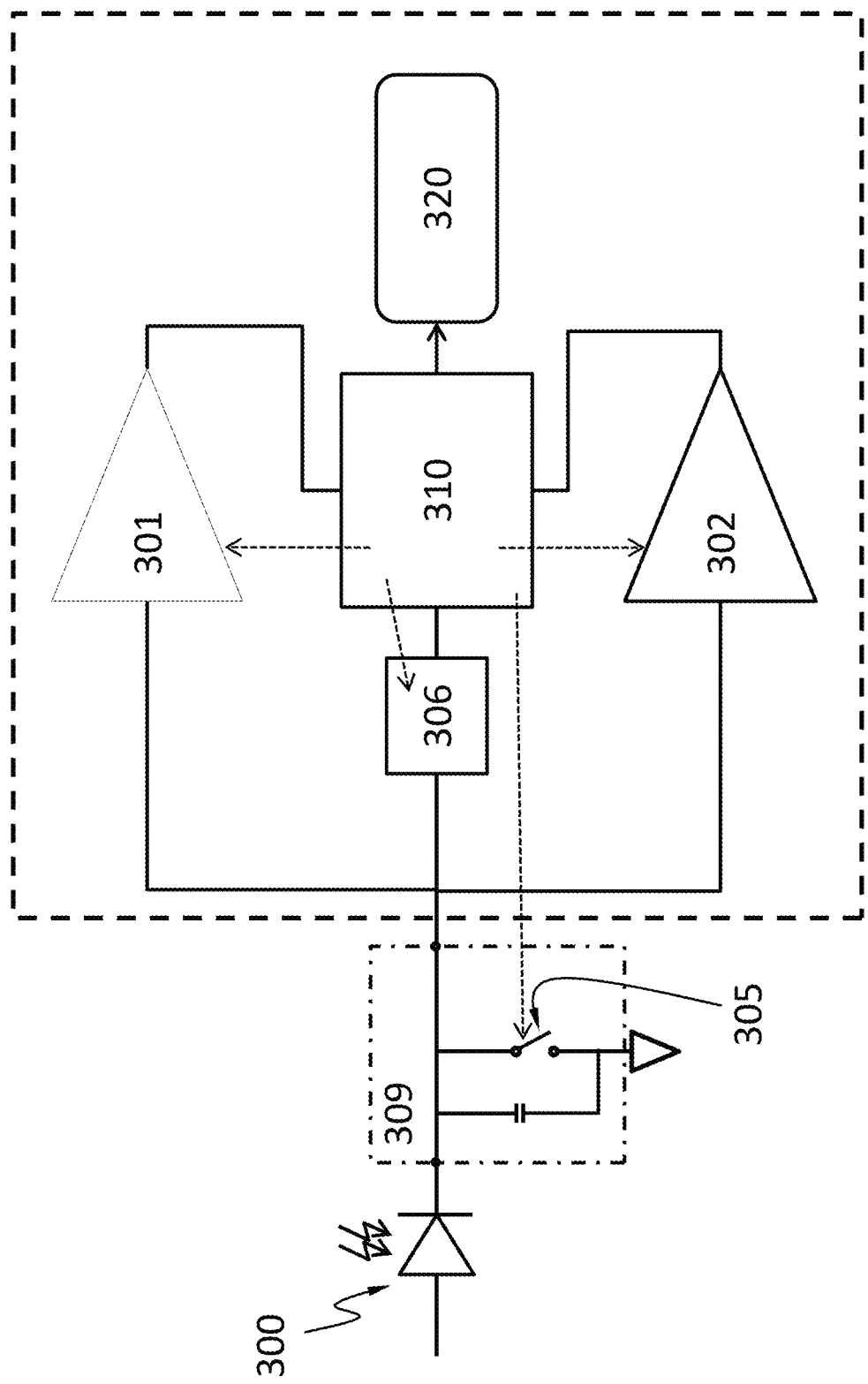

FIG. 10A and FIG. 10B each show a component diagram of the electronics system 121, according to an embodiment. The electronics system 121 may include a first voltage comparator 301, a second voltage comparator 302, a counter 320, a switch 305, a voltmeter 306 and a controller 310.

The first voltage comparator 301 is configured to compare the voltage of an electrode of a diode 300 to a first threshold. The diode may be a diode formed by the first doped region 111, one of the discrete regions 114 of the second doped region 113, and the optional intrinsic region 112. Alternatively, the first voltage comparator 301 is configured to compare the voltage of an electrical contact (e.g., a discrete portion of electrical contact 119B) to a first threshold. The first voltage comparator 301 may be configured to monitor the voltage directly, or calculate the voltage by integrating an electric current flowing through the diode or electrical contact over a period of time. The first voltage comparator 301 may be controllably activated or deactivated by the controller 310. The first voltage comparator 301 may be a continuous comparator. Namely, the first voltage comparator 301 may be configured to be activated continuously, and monitor the voltage continuously. The first voltage comparator 301 configured as a continuous comparator reduces the chance that the system 121 misses signals generated by an incident X-ray photon. The first voltage comparator 301 configured as a continuous comparator is especially suitable when the incident X-ray intensity is relatively high. The first voltage comparator 301 may be a clocked comparator, which has the benefit of lower power consumption. The first voltage comparator 301 configured as a clocked comparator may cause the system 121 to miss signals generated by some incident X-ray photons. When the incident X-ray intensity is low, the chance of missing an incident X-ray photon is low because the time interval between two successive photons is relatively long. Therefore, the first voltage comparator 301 configured as a clocked comparator is especially suitable when the incident X-ray intensity is relatively low. The first threshold may be 5-10%, 10%-20%, 20-30%, 30-40% or 40-50% of the maximum voltage one incident X-ray photon may generate in the diode or the resistor. The maximum voltage may depend on the energy of the incident X-ray photon (i.e., the wavelength of the incident X-ray), the material of the X-ray absorption layer 110, and other factors. For example, the first threshold may be 50 mV, 100 mV, 150 mV, or 200 mV.

The second voltage comparator 302 is configured to compare the voltage to a second threshold. The second voltage comparator 302 may be configured to monitor the voltage directly, or calculate the voltage by integrating an electric current flowing through the diode or the electrical contact over a period of time. The second voltage comparator 302 may be a continuous comparator. The second voltage comparator 302 may be controllably activate or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, & \text{if } x \geq 0 \\ -x, & \text{if } x \leq 0 \end{cases}.$$

The second threshold may be 200%-300% of the first threshold. The second threshold may be at least 50% of the maximum voltage one incident X-ray photon may generate in the diode or resistor. For example, the second threshold may be 100 mV, 150 mV, 200 mV, 250 mV or 300 mV. The second voltage comparator 302 and the first voltage comparator 310 may be the same component. Namely, the system 121 may have one voltage comparator that can compare a voltage with two different thresholds at different times.

The first voltage comparator 301 or the second voltage comparator 302 may include one or more op-amps or any other suitable circuitry. The first voltage comparator 301 or the second voltage comparator 302 may have a high speed to allow the system 121 to operate under a high flux of incident X-ray. However, having a high speed is often at the cost of power consumption.

The counter 320 is configured to register a number of X-ray photons reaching the diode or resistor. The counter 320 may be a software component (e.g., a number stored in a computer memory) or a hardware component (e.g., a 4017 IC and a 7490 IC).

The controller 310 may be a hardware component such as a microcontroller and a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electrical contact is used. The controller 310 may be configured to keep deactivated the second voltage comparator 302, the counter 320 and any other circuits the operation of the first voltage comparator 301 does not require, before the time at which the first voltage comparator 301 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero" means that temporal change of the voltage is less than 0.1%/ns. The phase "the rate of change of the voltage is substantially non-zero" means that temporal change of the voltage is at least 0.1%/ns.

The controller 310 may be configured to activate the second voltage comparator during (including the beginning and the expiration) the time delay. In an embodiment, the controller 310 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to cause the number registered by the counter 320 to increase by one, if, during the time delay, the second voltage comparator 302 determines that the absolute value of the voltage equals or exceeds the absolute value of the second threshold.

The controller 310 may be configured to cause the voltmeter 306 to measure the voltage upon expiration of the time delay. The controller 310 may be configured to connect the electrode to an electrical ground, so as to reset the voltage and discharge any charge carriers accumulated on the electrode. In an embodiment, the electrode is connected to an electrical ground after the expiration of the time delay. In an embodiment, the electrode is connected to an electrical ground for a finite reset time period. The controller 310 may connect the electrode to the electrical ground by controlling the switch 305. The switch may be a transistor such as a field-effect transistor (FET).

In an embodiment, the system 121 has no analog filter network (e.g., a RC network). In an embodiment, the system 121 has no analog circuitry.

The voltmeter 306 may feed the voltage it measures to the controller 310 as an analog or digital signal.

Figure 11:
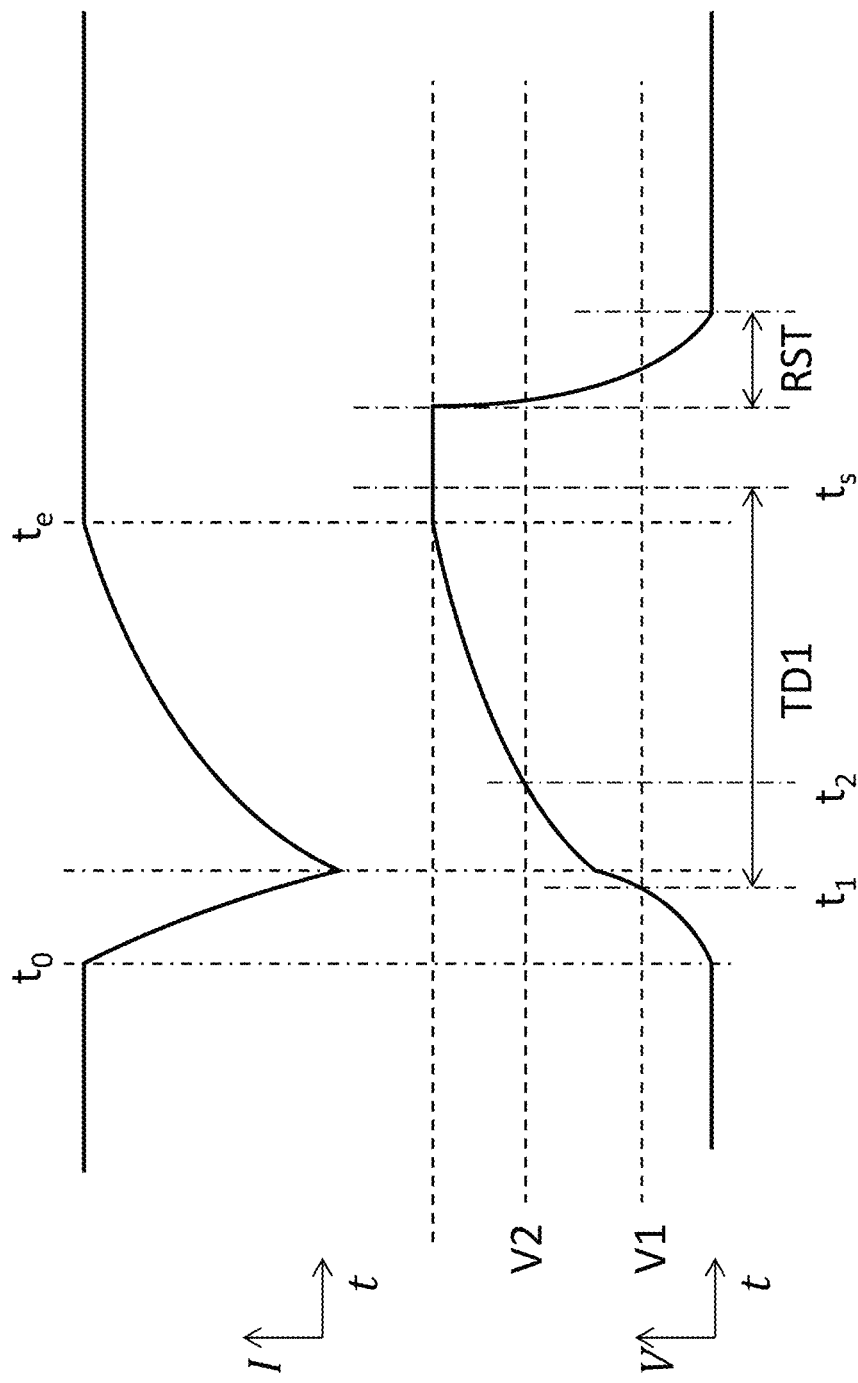
FIG. 11 schematically shows a temporal change of the electric current flowing through an electrode (upper curve) of a diode or an electrical contact of a resistor of an X-ray absorption layer exposed to X-ray, the electric current caused by charge carriers generated by an X-ray photon incident on the X-ray absorption layer, and a corresponding temporal change of the voltage of the electrode (lower curve), according to an embodiment.

The system 121 may include a capacitor module 309 electrically connected to the electrode of the diode 300 or which electrical contact, wherein the capacitor module is configured to collect charge carriers from the electrode. The capacitor module can include a capacitor in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path. Charge carriers from the electrode accumulate on the capacitor over a period of time ("integration period") (e.g., as shown in FIG. 11, between $t_0$ to $t_1$, or $t_1$-$t_2$). After the integration period has expired, the capacitor voltage is sampled and then reset by a reset switch. The capacitor module can include a capacitor directly connected to the electrode.

FIG. 11 schematically shows a temporal change of the electric current flowing through the electrode (upper curve) caused by charge carriers generated by an X-ray photon incident on the diode or the resistor, and a corresponding temporal change of the voltage of the electrode (lower curve). The voltage may be an integral of the electric current with respect to time. At time to, the X-ray photon hits the diode or the resistor, charge carriers start being generated in the diode or the resistor, electric current starts to flow through the electrode of the diode or the resistor, and the absolute value of the voltage of the electrode or electrical contact starts to increase. At time $t_1$, the first voltage comparator 301 determines that the absolute value of the voltage equals or exceeds the absolute value of the first threshold V1, and the controller 310 starts the time delay TD1 and the controller 310 may deactivate the first voltage comparator 301 at the beginning of TD1. If the controller 310 is deactivated before $t_1$, the controller 310 is activated at $t_1$. During TD1, the controller 310 activates the second voltage comparator 302. The term "during" a time delay as used here means the beginning and the expiration (i.e., the end) and any time in between. For example, the controller 310 may activate the second voltage comparator 302 at the expiration of TD1. If during TD1, the second voltage comparator 302 determines that the absolute value of the voltage equals or exceeds the absolute value of the second threshold at time $t_2$, the controller 310 causes the number registered by the counter 320 to increase by one. At time $t_e$, all charge carriers generated by the X-ray photon drift out of the X-ray absorption layer 110. At time $t_s$, the time delay TD1 expires. In the example of FIG. 11, time $t_s$ is after time $t_e$; namely TD1 expires after all charge carriers generated by the X-ray photon drift out of the X-ray absorption layer 110. The rate of change of the voltage is thus substantially zero at $t_s$. The controller 310 may be configured to deactivate the second voltage comparator 302 at expiration of TD1 or at $t_2$, or any time in between.

The controller 310 may be configured to cause the voltmeter 306 to measure the voltage upon expiration of the time delay TD1. In an embodiment, the controller 310 causes the voltmeter 306 to measure the voltage after the rate of change of the voltage becomes substantially zero after the expiration of the time delay TD1. The voltage at this moment is proportional to the amount of charge carriers generated by an X-ray photon, which relates to the energy of the X-ray photon. The controller 310 may be configured to determine the energy of the X-ray photon based on voltage the voltmeter 306 measures. One way to determine the energy is by binning the voltage. The counter 320 may have a sub-counter for each bin. When the controller 310 determines that the energy of the X-ray photon falls in a bin, the controller 310 may cause the number registered in the sub-counter for that bin to increase by one. Therefore, the system 121 may be able to detect an X-ray image and may be able to resolve X-ray photon energies of each X-ray photon.

After TD1 expires, the controller 310 connects the electrode to an electric ground for a reset period RST to allow charge carriers accumulated on the electrode to flow to the ground and reset the voltage. After RST, the system 121 is ready to detect another incident X-ray photon. Implicitly, the rate of incident X-ray photons the system 121 can handle in the example of FIG. 11 is limited by 1/(TD1+RST). If the first voltage comparator 301 has been deactivated, the controller 310 can activate it at any time before RST expires. If the controller 310 has been deactivated, it may be activated before RST expires.

Figure 12:
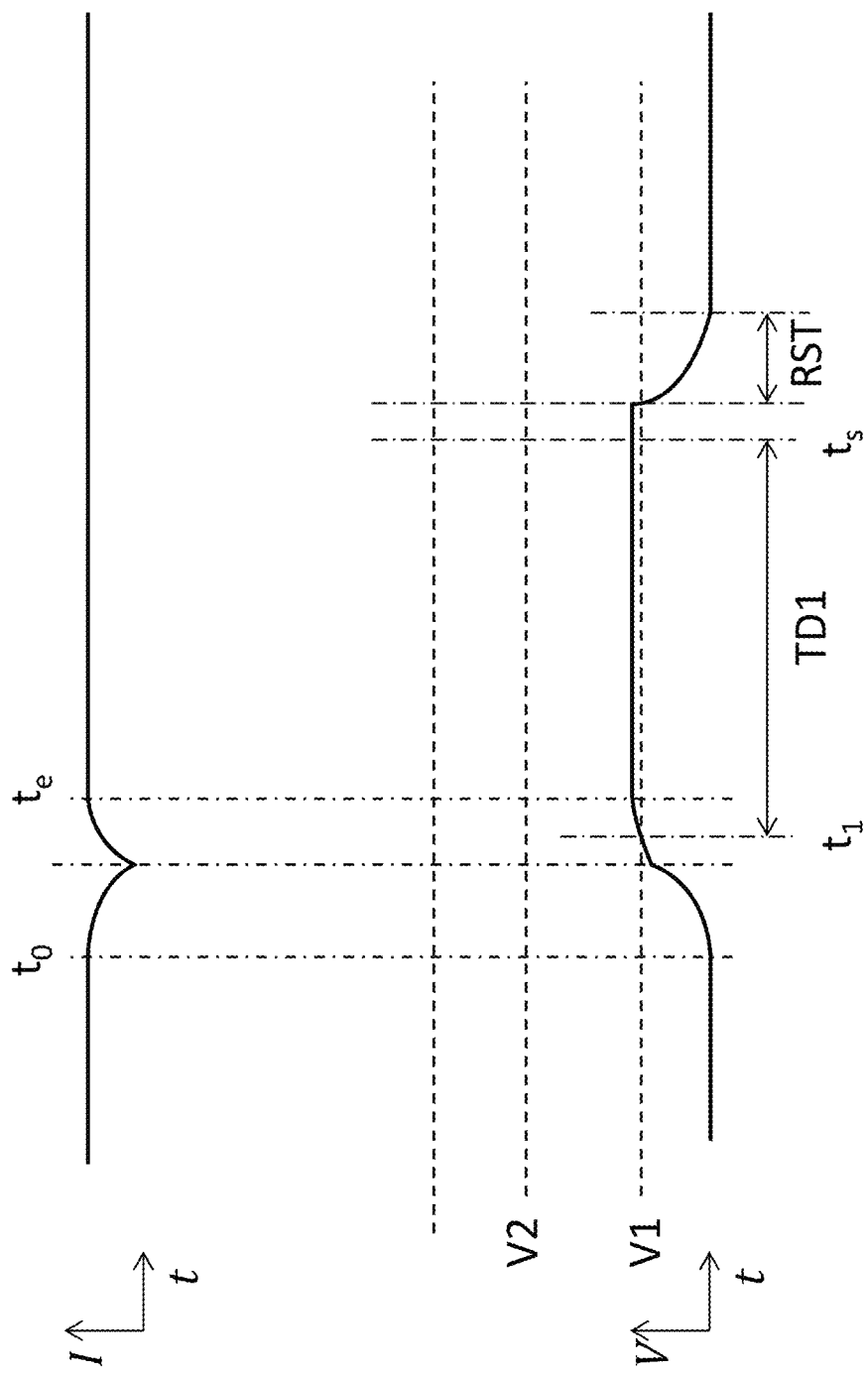
FIG. 12 schematically shows a temporal change of the electric current flowing through the electrode (upper curve) caused by noise (e.g., dark current), and a corresponding temporal change of the voltage of the electrode (lower curve), in the electronics system operating in the way shown in FIG. 8, according to an embodiment.

FIG. 12 schematically shows a temporal change of the electric current flowing through the electrode (upper curve) caused by noise (e.g., dark current, background radiation, scattered X-rays, fluorescent X-rays, shared charges from adjacent pixels), and a corresponding temporal change of the voltage of the electrode (lower curve), in the system 121 operating in the way shown in FIG. 11. At time to, the noise begins. If the noise is not large enough to cause the absolute value of the voltage to exceed the absolute value of V1, the controller 310 does not activate the second voltage comparator 302. If the noise is large enough to cause the absolute value of the voltage to exceed the absolute value of V1 at time $t_1$ as determined by the first voltage comparator 301, the controller 310 starts the time delay TD1 and the controller 310 may deactivate the first voltage comparator 301 at the beginning of TD1. During TD1 (e.g., at expiration of TD1), the controller 310 activates the second voltage comparator 302. The noise is very unlikely large enough to cause the absolute value of the voltage to exceed the absolute value of V2 during TD1. Therefore, the controller 310 does not cause the number registered by the counter 320 to increase. At time $t_e$, the noise ends. At time $t_s$, the time delay TD1 expires. The controller 310 may be configured to deactivate the second voltage comparator 302 at expiration of TD1. The controller 310 may be configured not to cause the voltmeter 306 to measure the voltage if the absolute value of the voltage does not exceed the absolute value of V2 during TD1. After TD1 expires, the controller 310 connects the electrode to an electric ground for a reset period RST to allow charge carriers accumulated on the electrode as a result of the noise to flow to the ground and reset the voltage. Therefore, the system 121 may be very effective in noise rejection.

Figure 13:
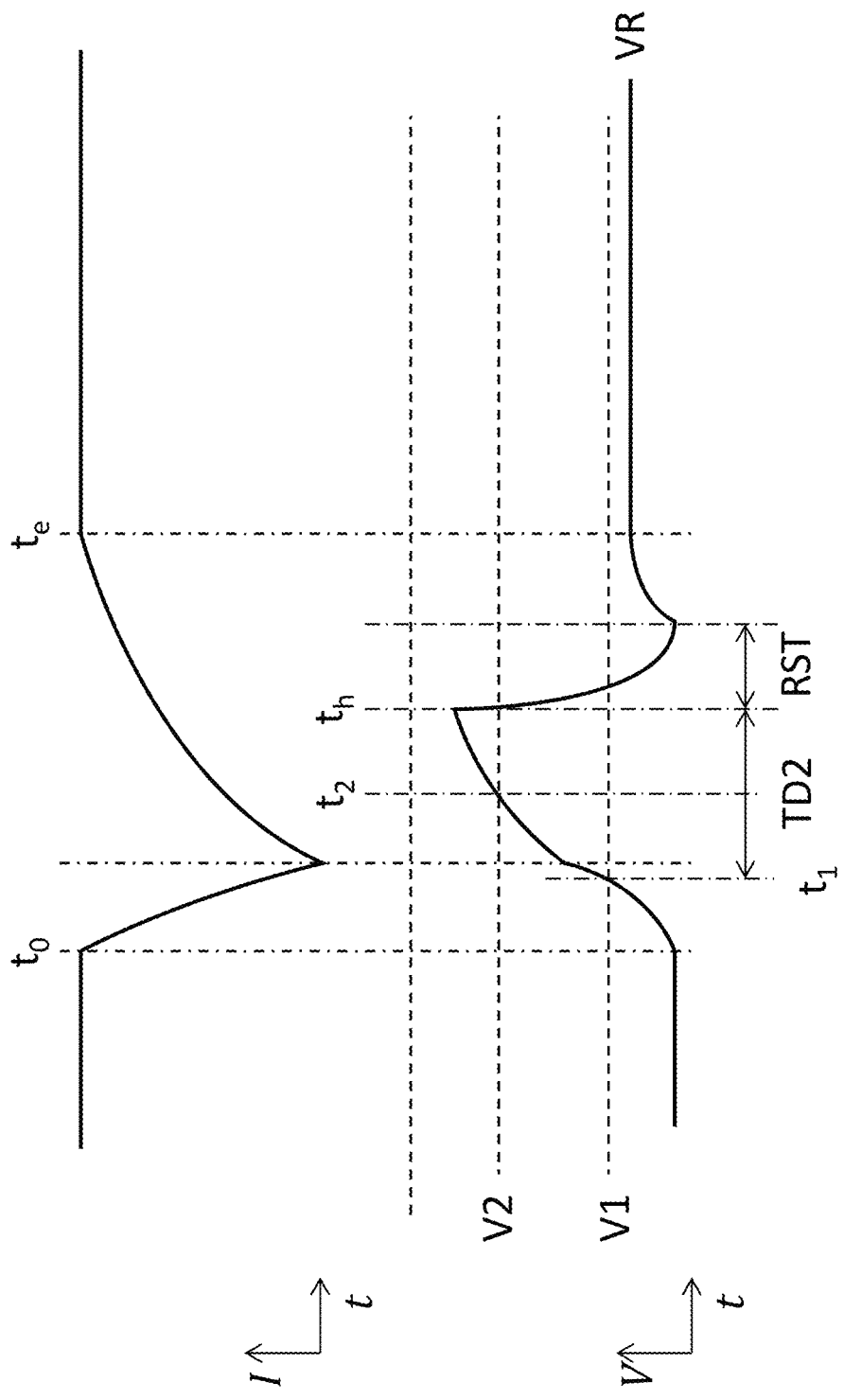
FIG. 13 schematically shows a temporal change of the electric current flowing through an electrode (upper curve) of the X-ray absorption layer exposed to X-ray, the electric current caused by charge carriers generated by an X-ray photon incident on the X-ray absorption layer, and a corresponding temporal change of the voltage of the electrode (lower curve), when the electronics system operates to detect incident X-ray photons at a higher rate, according to an embodiment.

FIG. 13 schematically shows a temporal change of the electric current flowing through the electrode (upper curve) caused by charge carriers generated by an X-ray photon incident on the diode or the resistor, and a corresponding temporal change of the voltage of the electrode (lower curve), when the system 121 operates to detect incident X-ray photons at a rate higher than 1/(TD1+RST). The voltage may be an integral of the electric current with respect to time. At time to, the X-ray photon hits the diode or the resistor, charge carriers start being generated in the diode or the resistor, electric current starts to flow through the electrode of the diode or the electrical contact of resistor, and the absolute value of the voltage of the electrode or the electrical contact starts to increase. At time $t_1$, the first voltage comparator 301 determines that the absolute value of the voltage equals or exceeds the absolute value of the first threshold V1, and the controller 310 starts a time delay TD2 shorter than TD1, and the controller 310 may deactivate the first voltage comparator 301 at the beginning of TD2. If the controller 310 is deactivated before $t_1$, the controller 310 is activated at $t_1$. During TD2 (e.g., at expiration of TD2), the controller 310 activates the second voltage comparator 302. If during TD2, the second voltage comparator 302 determines that the absolute value of the voltage equals or exceeds the absolute value of the second threshold at time $t_2$, the controller 310 causes the number registered by the counter 320 to increase by one. At time $t_e$, all charge carriers generated by the X-ray photon drift out of the X-ray absorption layer 110. At time th, the time delay TD2 expires. In the example of FIG. 13, time th is before time $t_e$; namely TD2 expires before all charge carriers generated by the X-ray photon drift out of the X-ray absorption layer 110. The rate of change of the voltage is thus substantially non-zero at $t_h$. The controller 310 may be configured to deactivate the second voltage comparator 302 at expiration of TD2 or at $t_2$, or any time in between.

The controller 310 may be configured to extrapolate the voltage at $t_e$ from the voltage as a function of time during TD2 and use the extrapolated voltage to determine the energy of the X-ray photon.

After TD2 expires, the controller 310 connects the electrode to an electric ground for a reset period RST to allow charge carriers accumulated on the electrode to flow to the ground and reset the voltage. In an embodiment, RST expires before $t_e$. The rate of change of the voltage after RST may be substantially non-zero because all charge carriers generated by the X-ray photon have not drifted out of the X-ray absorption layer 110 upon expiration of RST before $t_e$. The rate of change of the voltage becomes substantially zero after $t_e$ and the voltage stabilized to a residue voltage VR after $t_e$. In an embodiment, RST expires at or after $t_e$, and the rate of change of the voltage after RST may be substantially zero because all charge carriers generated by the X-ray photon drift out of the X-ray absorption layer 110 at $t_e$. After RST, the system 121 is ready to detect another incident X-ray photon. If the first voltage comparator 301 has been deactivated, the controller 310 can activate it at any time before RST expires. If the controller 310 has been deactivated, it may be activated before RST expires.

Figure 14:
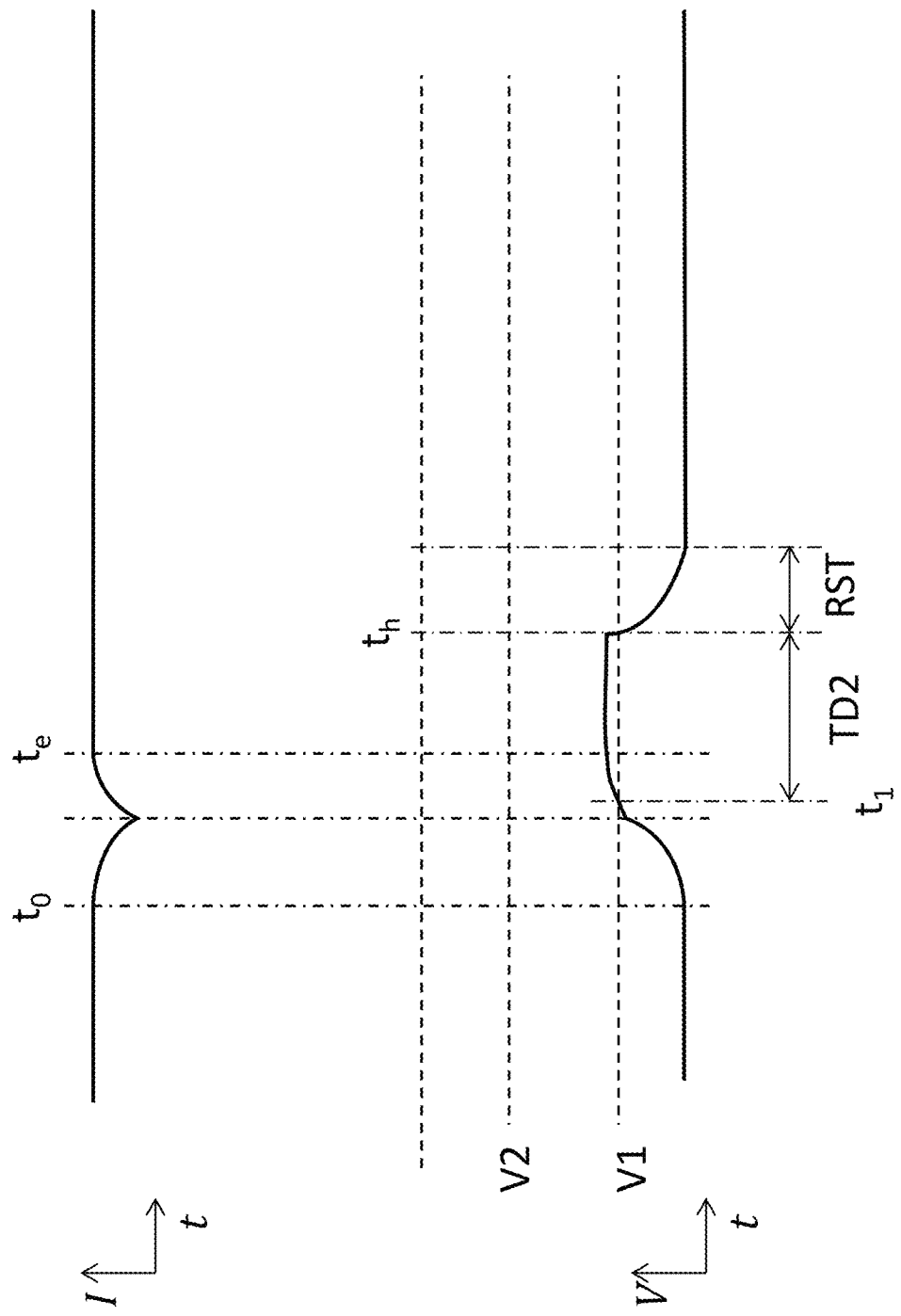
FIG. 14 schematically shows a temporal change of the electric current flowing through the electrode (upper curve) caused by noise (e.g., dark current), and a corresponding temporal change of the voltage of the electrode (lower curve), in the electronics system operating in the way shown in FIG. 10A or FIG. 10B, according to an embodiment.

FIG. 14 schematically shows a temporal change of the electric current flowing through the electrode (upper curve) caused by noise (e.g., dark current, background radiation, scattered X-rays, fluorescent X-rays, shared charges from adjacent pixels), and a corresponding temporal change of the voltage of the electrode (lower curve), in the system 121 operating in the way shown in FIG. 13. At time to, the noise begins. If the noise is not large enough to cause the absolute value of the voltage to exceed the absolute value of V1, the controller 310 does not activate the second voltage comparator 302. If the noise is large enough to cause the absolute value of the voltage to exceed the absolute value of V1 at time $t_1$ as determined by the first voltage comparator 301, the controller 310 starts the time delay TD2 and the controller 310 may deactivate the first voltage comparator 301 at the beginning of TD2. During TD2 (e.g., at expiration of TD2), the controller 310 activates the second voltage comparator 302. The noise is very unlikely large enough to cause the absolute value of the voltage to exceed the absolute value of V2 during TD2. Therefore, the controller 310 does not cause the number registered by the counter 320 to increase. At time $t_e$, the noise ends. At time $t_h$, the time delay TD2 expires. The controller 310 may be configured to deactivate the second voltage comparator 302 at expiration of TD2. After TD2 expires, the controller 310 connects the electrode to an electric ground for a reset period RST to allow charge carriers accumulated on the electrode as a result of the noise to flow to the ground and reset the voltage. Therefore, the system 121 may be very effective in noise rejection.

Figure 15:
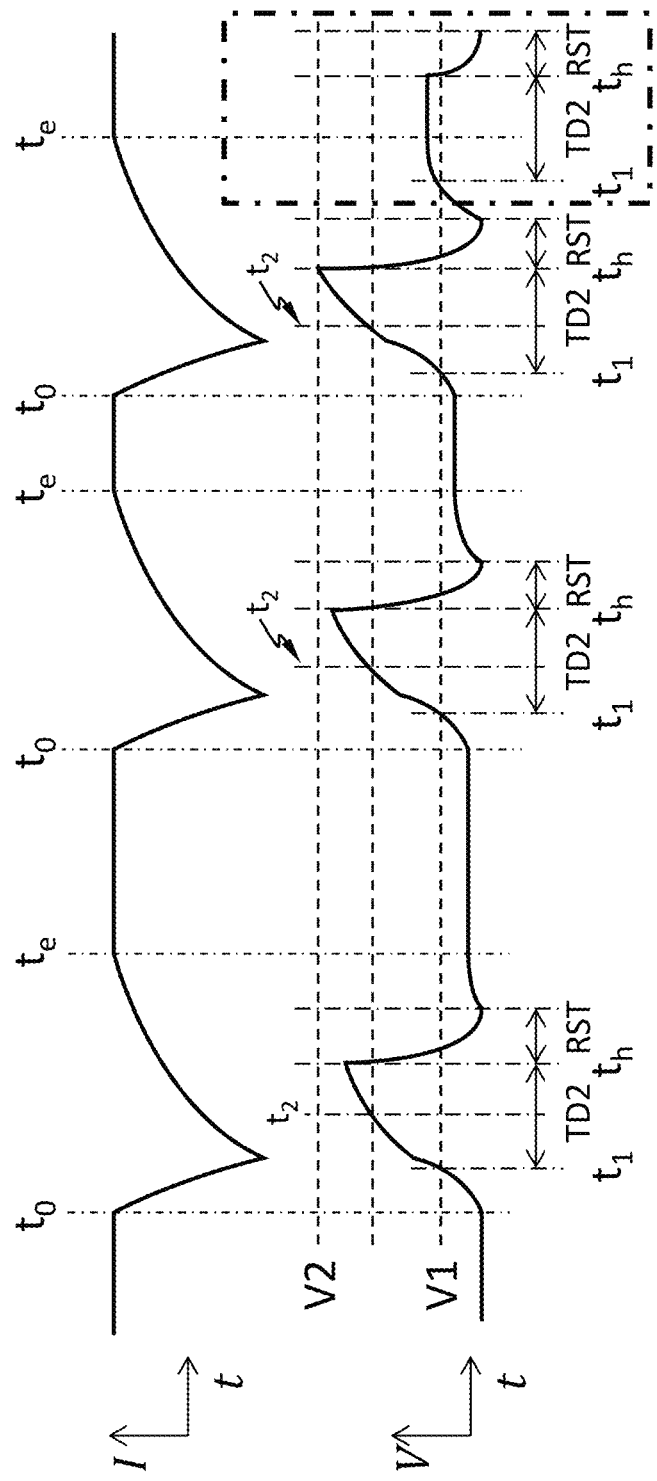
FIG. 15 schematically shows a temporal change of the electric current flowing through the electrode (upper curve) caused by charge carriers generated by a series of X-ray photons incident on the X-ray absorption layer, and a corresponding temporal change of the voltage of the electrode, in the electronics system operating in the way shown in FIG. 10A or FIG. 10B with RST expires before $t_e$, according to an embodiment.

FIG. 15 schematically shows a temporal change of the electric current flowing through the electrode (upper curve) caused by charge carriers generated by a series of X-ray photons incident on the diode or the resistor, and a corresponding temporal change of the voltage of the electrode (lower curve), in the system 121 operating in the way shown in FIG. 13 with RST expires before $t_e$. The voltage curve caused by charge carriers generated by each incident X-ray photon is offset by the residue voltage before that photon. The absolute value of the residue voltage successively increases with each incident photon. When the absolute value of the residue voltage exceeds V1 (see the dotted rectangle in FIG. 15), the controller starts the time delay TD2 and the controller 310 may deactivate the first voltage comparator 301 at the beginning of TD2. If no other X-ray photon incidence on the diode or the resistor during TD2, the controller connects the electrode to the electrical ground during the reset time period RST at the end of TD2, thereby resetting the residue voltage. The residue voltage thus does not cause an increase of the number registered by the counter 320.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system comprising:
 a first layer,
 a second layer with a temperature driver therein,
 a controller comprising a processor and a memory, the memory having a program stored therein, the processor configured to control powers to the temperature driver by executing the program;
 wherein the program, when executed, causes the processor to set powers to the temperature driver such that relative thermal expansions of the first layer and the second layer are essentially the same at all time during a process of bonding the first layer and the second layer.

2. The system of claim 1, wherein the first layer is an X-ray absorption layer configured to absorb X-ray photons; wherein the second layer is an electronics layer comprising an electronics system configured to process or interpret signals generated by the X-ray photons.

3. The system of claim 1, further comprising a support; wherein the second layer is mounted to the support and the controller controls the powers to the temperature driver through an electrical contact on the support.

4. The system of claim 1, wherein the second layer comprises a temperature sensor.

5. The system of claim 4, wherein the controller reads temperature of the second layer from the temperature sensor and controls the powers to the temperature driver in the second layer based on the temperature read from the temperature sensor.

* * * * *